ical Engineering IEEE USA, vol. 49, No. 9, Sep. 2002, pp.
United States Patent
Grohovaz et al.

(10) Patent No.: US 9,274,100 B2
(45) Date of Patent: Mar. 1, 2016

(54) METHOD FOR OPTICAL MEASURING VARIATIONS OF CELL MEMBRANE CONDUCTANCE

(75) Inventors: Fabio Grohovaz, Milan (IT); Stefano Pitassi, Udine (IT); Andrea Domenico Menegon, Milan (IT)

(73) Assignee: OSPEDALE SAN RAFFAELE S.R.L., Milan (IT)

( * ) Notice: Subject to any disclaimer, the term of this patent is extended or adjusted under 35 U.S.C. 154(b) by 995 days.

(21) Appl. No.: 13/386,225

(22) PCT Filed: Jul. 16, 2010

(86) PCT No.: PCT/EP2010/060362
§ 371 (c)(1),
(2), (4) Date: Feb. 29, 2012

(87) PCT Pub. No.: WO2011/009825
PCT Pub. Date: Jan. 27, 2011

(65) Prior Publication Data
US 2012/0149052 A1    Jun. 14, 2012

(30) Foreign Application Priority Data
Jul. 20, 2009 (EP) .................................. 09165872

(51) Int. Cl.
*G01N 33/50* (2006.01)
*G01N 33/68* (2006.01)
*G01N 33/487* (2006.01)

(52) U.S. Cl.
CPC ........ *G01N 33/5008* (2013.01); *G01N 33/6872* (2013.01); *G01N 33/48728* (2013.01); *G01N 33/48735* (2013.01)

(58) Field of Classification Search
None
See application file for complete search history.

(56) References Cited

U.S. PATENT DOCUMENTS

| 6,331,438 | B1 * | 12/2001 | Aylott et al. | ................... 436/172 |
| 2002/0025568 | A1 * | 2/2002 | Maher | ................ G01N 33/5008 |
| | | | | 435/173.6 |
| 2003/0170898 | A1 * | 9/2003 | Gundersen et al. | ........... 435/461 |
| 2005/0226816 | A1 * | 10/2005 | Diwu et al. | .................... 424/9.6 |

FOREIGN PATENT DOCUMENTS

WO    2004/012585 A2    2/2004

OTHER PUBLICATIONS

Pucihar, G et al. Numerical determination of transmembrane voltage induced on irregularly shaped cells. Annals of Biomedical Engineering. 2006. 34(4): 642-652.*
Mel, et al.: "Can optical recordings of membrane potential be used to screen for drug-induced action potential prolongation in single cardiac myocytes?", Journal of Pharmacological and Toxicological Methods , Elsevier , New York, NY , vol. 54, No. 2, Sep. 1, 2006, pp. 173-182, ISSN: 1056-8719, [retrieved on Sep. 1, 2006].
Sharma V et al: "Decomposition of field-induced transmembrane potential responses of single cardiac cells", IEEE Transactions on Biomedical Engineering IEEE USA, vol. 49, No. 9, Sep. 2002, pp. 1031-1037, ISSN : 0018-9294.
Knopfel, et al.: "Optical recordings of membrane potential using genetically targeted voltage-sensitive fluorescent proteins", Methods (Orlando), vol. 30, No. 1, May 2003, pp. 42-48, ISSN: 1046-2023.

* cited by examiner

*Primary Examiner* — Renee Claytor
*Assistant Examiner* — Susan E Fernandez
(74) *Attorney, Agent, or Firm* — Lucas & Mercanti, LLP.

(57) ABSTRACT

The instant invention refers to an optical method to extrapolate cell membrane conductance by indirect measurement of changes in transmembrane voltage, upon exposure of a cell sample to electric current pulses. The method is advantageously used for evaluating the activity of molecules able to alter, directly or indirectly, membrane permeability. A specific field of application is the screening of candidate compounds putatively acting on ion channel activity. In particular, it is open to the study of all ion channels with no limitations on the mechanisms of activation or to the ion species involved. The method is also advantageously used for evaluating a cell status, namely a differentiative or a pathologic status.

17 Claims, 8 Drawing Sheets

METHOD FOR OPTICAL MEASURING VARIATIONS OF CELL MEMBRANE CONDUCTANCE

CROSS-REFERENCE TO RELATED APPLICATIONS

This application is a 371 of PCT/EP2010/060362, filed Jul. 16, 2010, which claims the benefit of European Patent Application No. 09165872.4, filed Jul. 20, 2009, the contents of each of which are incorporated herein by reference.

TECHNICAL FIELD

The instant invention refers to an optical method to extrapolate cell membrane conductance by indirect measurement of changes in transmembrane voltage, upon exposure of a cell sample to electric current pulses. The method is advantageously used for evaluating the activity of molecules able to alter, directly or indirectly, membrane permeability. A specific field of application is the screening of candidate compounds putatively acting on ion channel activity. Of note, the method applies to any type of channels (no matter the mechanism of activation) or transporters able to significantly change membrane permeability. The method is also advantageously used for evaluating a cell status, namely a differentiative or a pathologic status.

BACKGROUND

Cell Membrane and Ion Channels

Cell membranes are composed of a lipid bilayer and a number of proteins, including ion channels. Accordingly, membranes exhibit both capacitive and resistive responses. Capacitive properties remain fairly constants, while resistive responses depend on the number and type of channels that are open.

Every cell shows a difference in potential between the aqueous solutions on the opposite sides of the plasma membrane. This transmembrane potential is sustained by the selective permeability of the membrane to ions as well as by the activity of electrogenic pumps. It follows that cytosolic ion concentration is tightly controlled with respect to the extracellular environment. On the one hand, this sets the conditions to trigger and propagate bioelectric events in specialized cells and, on the other hand, it sustains controlled changes in the cytosolic ionic concentrations, an important and ubiquitous mechanism of intracellular signalling. The measurement of transmembrane potential, traditionally performed via insertion of an electrode in the cell, has been the starting point to investigate the variation in membrane permeability or, equivalently, its conductance. Such equivalence between biological and electric parameters is motivated by the representation of the cell membrane as a dielectric material (lipid bilayer) that is essentially impermeable to most charged molecules, and causes the membrane to act as a capacitor by separating the charges lying along its interior and exterior surfaces. The opening of selective aqueous pores within transmembrane proteins (ion channels) enables specific ions to move in and out the cell, down their electrochemical gradient, thus temporarily or steadily modifying the membrane conductance.

Ion channels are generally classified according to either their ion selectivity ($K^+$, $Na^+$, $Ca^2$, $Cl^-$) or the type of activation mechanism. According to the latter criterion, main gating mechanisms of ion channel opening can be classified as:

binding of molecules (either in the extracellular or intracellular milieu);
changes in transmembrane potential;
mechanical strain of the cell membrane.

Cellular permeability is determined by both the type and the number of ion channels present and active in the plasma membrane Recent evidence shows that the expression of channels can be determined not only by the control of their biosynthesis but also by local recycling between inner compartments and cell surface, thereby permitting the rapid adaptation of their functional expression in response to specific signals. Moreover, biologically active molecules whose activity is expressed after their incorporation into the membrane bilayer induce the formation of pores with variable levels of ionic selectivity. This is the case of some antibiotics showing an ohmic behaviour (such as nistatin, amphotericin B, gramicidin) or non-ohmic behaviour (such as alameticin).

The control of ion fluxes (and consequently the membrane permeability) is fundamental for cell life as well as for main cellular functions (neurotransmitters/hormones release, excitability control, gene activation etc.); then it is evident that any alteration of the ionic balance can have important consequences on cell physiology. The wide interest in this field is documented by the introduction of the term "channelopathies" to include all the diseases associated with mutations of ion channels subunits. Therefore, there is the need for an easy and fast screening of candidate compounds able to modulate membrane permeability/conductance by specifically affecting ion channel activities and then acting as channelopathies drugs.

DETECTION TECHNOLOGIES OF PRIOR ART

At the moment, among 100 top-selling drugs, 15 are ion-channel modulators. However, despite the scientific, social, and even commercial relevance of ion channel drugs, the process of their discovery suffers of intrinsic problems. From a physiological viewpoint, the final activity promoted by these compounds does not necessarily reflect the real extent of channel activation, since it often involves a cascade of events, with either reinforcement or inhibition of the response according to cell conditions. On the other hand, their pharmacological targets (ion channels) show a variety of different conformational states, thus increasing the probability of interactions with channels other than those of interest. In the attempt to overcome these difficulties, the new frontier of research is focused on the discovery of selective state-dependent drugs, targeted to specific ion channels.

Accordingly, the identification of highly-selective drugs demands for screening technologies able to:
isolate the contribution of a specific ion channel (highly specific readout response);
detect the direct effect of the compound under investigation on ion channel activation (high time resolution);
discriminate responses with subcellular resolution, thereby enabling the use of cellular models with heterogeneous composition as well as the analysis of effects in discrete subcompartments (high spatial resolution).

The first issue is generally addressed by selecting, modifying and reprogramming cells to specifically express the ion channel of interest, also avoiding cross-responses of other receptors/channels. More critical is the second issue, since several assays have been proposed to evaluate ion channel activity but no gold standard is available. In general, they are comprised between two extreme points:

assays with relatively low information content, low cost and high throughput: High-Throughput Screening (HTS);

assays with high information content but low throughput and high costs: High-Content Screening (HCS).

The study of ion fluxes provides a direct measure of channel activity, even though the available techniques pose some challenges. The use of radioactive isotopes is expensive; it raises safety problems and is characterized by low temporal resolution and low throughput. Atomic absorption spectroscopy allows medium throughput screening but is limited to the study of $K^+$ and non-selective cation channels; moreover, $K^+$ flux is integrated over time, thereby leading to an underestimation of the drug potency. On the other hand, ion-luminescence or ion-fluorescence detection systems are compatible with HTS studies but have low temporal resolution, are virtually confined to the study of changes in calcium concentration and can be spoiled by superimposition of signals related to calcium released from intracellular stores.

In order to overcome the intrinsic limitations of these approaches, thus obtaining better qualitative and quantitative information on candidate molecules, industry has turned the attention back to electrophysiology.

Manual patch-clamp is indeed efficient in probing ion channel activity, as it can measure small ion currents with sub-millisecond temporal resolution while controlling the membrane potential, but suffers from being too slow, complex and expensive; moreover it requires the active contribution of highly skilled personnel. Some improvements have been recently achieved with automated patch-clamp (APC) instrumentation, even though they are still far away from being classified as HTS methods.

Recently, optical technologies have been introduced to investigate the ion channel responses to activation stimuli by detecting changes in the membrane potential. These kinds of assays currently account for approximately 40% of the total market of optical probes used in ion channel HTS, and appears to be the most dynamic and promising among emerging technologies. In essence, they use optical voltage sensors whose read-out is determined by the values of membrane potential, and thus by the conditions of channel gating (open or close). They can be classified into two different classes of dyes, each showing specific features:

Fast response Voltage-Sensitive Dyes (fast-VSD) undergo electrical field-triggered molecular rearrangements with a consequent change of their optical properties. Their response is extremely rapid and enables measurements of transient potential changes on a millisecond time scale. Their main limitation is low sensitivity (e.g. a change in signal value<10%/100 mV). Sensitivity improvements have been reported for ANNINE-6 or ANNINE-6plus (about 35%/100 mV), but with limitations concerning photostability and solubility. Fast-VSD have been used to monitor the membrane potential changes following transition of channels to an ion-conducting state. However, despite their fast kinetic, fast-VSDs are not used for screening approaches as moderate variations can be hardly detected due to their limited sensitivity. Intramolecular FRET based molecules have been developed in order to combine high sensitivity with fast-responding characteristics. Unfortunately this method is still inadequate for screening because these molecules induce profound physiological alterations.

Slow response Voltage-Sensitive Dyes (slow-VSD) are characterized by slow temporal resolutions (typically tens of seconds), due to the transmembrane migration of the entire molecule. They show higher sensitivities (about 100%/100 mV for rhodamine, merocyanine and oxonol) and are commonly used in HTS screening. Despite new developments in the design of intermolecular VSD fluorescence probes (based on the use of quenchers or intermolecular FRET) temporal responses are still much longer than ion channel kinetics However, despite the remarkable improvements, measures with slow-VSD dyes still suffer from various limitations: time resolution (seconds), spatial resolution (populations of cells), information content, kind of ionic channels that can be investigated (voltage gated or channels leading to remarkable potential changes).

From the above considerations, it may be concluded that:

Ion channels have considerable attractiveness as drug discovery targets for a variety of pathologies, including the central nervous and cardiovascular systems.

Optical methods have the advantage of being simpler, non-invasive and cheap, but they are currently inadequate to monitor ion channel properties with high time resolution.

Despite the continuous efforts at developing platforms that utilize automated electrophysiological techniques, the demand for higher throughput is not satisfied being expensive and far from HTS standard.

The method of WO 02/087489 (EP 1303757) rests on the presence and the activation of at least one type of voltage-operated channel. The method discloses instrumentation and methods for modulating the transmembrane potentials of living cells in order to specifically elicit the opening of voltage-operated ion channels. Once opened, their activity is optically monitored by a fluorescence-based approach. Instrumentation includes electrodes and electrode arrays for generating uniform electric fields which are time modulated in order to regulate the activation states of voltage-operated ion channels present within the cells, thereby cycling them through resting, activated and inactivated states. By applying a repetitive train of electric stimuli, separated by a time interval smaller than the membrane time constant, it is possible to raise the average transmembrane potential in an approximately stepwise fashion. The method bases its stimulations on imposing trains of short biphasic pulses (0.1-20 ms duration each) that cause voltage-operated ion channels to open or to be released from inactivation. In the instant invention the electric stimulus (either mono or bipolar and with a duration >20 ms) is not intended to open voltage-operated channels or to change their activation states; instead, it is intended to alter the driving force for ion fluxes across the plasma membrane. Therefore, this invention shows potential screening applications that require the presence of at least one type of voltage-operated channel while the instant invention, standing on a completely different theoretical ground, applies to any type of channels (no matter their mechanism of activation) or transporters able to significantly change membrane permeability. Moreover the document uses methods wherein the stimulation is performed by imposing well defined voltages to the cells; in the instant invention the field potentials do not need to be uniform, so that stimulations are represented by electric currents. The document discloses the use of trains of electric field pulses that are repeated at a frequency of stimulation that is greater than or equal to the reciprocal of the transmembrane constant, whereas the instant invention makes use of a single pulse. The activity of a candidate compound is measured by a VSD approach and the fluorescence variations directly reflect the changes in potential caused by the $Na^+$ current elicited upon $Na^+$ channel opening induced by the trains of electric pulses. In the instant invention, electric pulses are not generated to open channels: the estimated fluorescence variations solely dependent on the imposed driving force for ion fluxes and the already established membrane conductance. Furthermore, differently from the document where "monitoring comprises detecting fluorescence emission from an area of observation containing said one or more cells", the instant invention is based on the estimation of the membrane conductance at the sub-cellular level (see "Detailed description of the invention"). WO 2004/012585 discloses a system that is capable of supplying electric field stimulation to a cell and optically monitoring a physiological response of the stimulated cell. The document also provides methods of eliciting a physiological response in a cell or characterizing the biological activity of a candidate compound using an electric field stimulation (EFS) device. Such methods are readily amenable to high throughput screen (HTS). The document uses methods wherein the stimulations is performed by imposing to the cells trains of voltage pulses with duration ranging from 250 µs to 1000 µs in the instant invention stimulations are represented by single pulses of electric current with a duration >20 ms. The document relies on the generation of a uniform field potential, whereas the field potential in the instant invention does not need to be uniform, so that electric current pulse are applied. The document simply compares the optical signals detected from all cells under investigation (cumulative effect), without specifying any method to extract physiological parameters from optical measurements; in the instant invention the membrane conductance at sub-cell level can be evaluated (see "Detailed description of the invention"). WO 2008/101128 refers to a method for assessing neural activity in a neural region having multiple subfields, the method comprising: evoking a cellular electric response in at least one subfield due to neural activity in the neural region; capturing image data of the cellular electric response at a level sufficiently detailed in space and time to differentiate between polarization-based events of two respective portions of the subfield; assessing neural activity by correlating space and time information, from the captured data, for the two respective portions of the sub-field. The document refers also to a method for assessing neural activity in a neuronal network that includes first and second portions electrically related to one another, the method comprising: staining the neuronal network with a voltage sensitive dye; stimulating the first portion of the neuronal network responsive to the stimulation; capturing image data resulting from the voltage sensitive dye and neural activity in the first portion; processing the image data to assess neural activity indicative of a disorder. The invention is solely intended for studying neuronal activity in brain slices. It uses electric stimulations in order to induce neuronal activity and monitor electric network responses.

WO 2005/014848 relates to a mammalian cell-based high-throughput assay for the profiling and screening of human epithelial sodium channel (hENaC) cloned from a human kidney c-DNA library and is also expressed in other tissues including human taste tissue. The document relates to amphibian oocyte-based medium-throughput electrophysiological assays for identifying human ENaC modulators, preferably ENaC enhancers. Compounds that modulate ENaC function in a cell-based ENaC assay are expected to affect salty taste in humans. The assays have advantages over existing cellular expression systems.

WO 2002/087306 relates to a mammalian cell-based high-throughput assay for the profiling and screening of human epithelial sodium channel (hENaC) cloned from a human kidney c-DNA library and is also expressed in other tissues including human taste tissue. It is thought that ENaC is involved in mediating mammalian salty taste responses. Compounds that modulates ENaC function in a cell-based ENaC assay would be expected to affect salty taste in humans. The present invention also provides recombinant mammalian cells that express a functional hENaC. Both WO 2005/014848 and WO 2002/087306 relate solely to assays that utilize test cells expressing a functional hENaC, and use conventional approaches (electrophysiology, slow-VSD or sodium-sensitive fluorescent dyes).

WO 2001/027253 refers to transmembrane potential measurement methods using cationic dyes, and anionic dyes. Compositions of the cationic and anionic dyes and microfluidic systems which include the dyes and membranes are provided in conjunction with processing elements for transmembrane potential measurements. The present invention uses neither fast-VSD nor electric stimulations, and is not capable of sub-cell analysis.

U.S. Pat. No. 6,979,553 refers to methods of measuring or monitoring changes in a transmembrane potential. In the methods, a first component which includes one or more membrane is flowed from a source to a first channel region. A labelling composition comprising a membrane permeable label is flowed into contact with the membrane. The membrane is altered in some way that causes an alteration in transmembrane potential, e.g., by changing the ionic composition on one side of the membrane (e.g., inside or outside of a cell) or by changing the permeability of the membrane to ions. The flow of the membrane permeable label across the membrane is monitored by monitoring a first signal output from the membrane permeable label, thereby measuring changes in the transmembrane potential. The document does not make use of stimulation.

WO 2002/042842 refers to a method for identifying a $Na^+$ channel blocker, including providing a cell containing a $Na^+$ channel blocker, demonstrating both a transient and a persistent current. The cell includes a potassium (K) channel and a Na/K AtPase ($Na^+$ pump). A fluorescent dye is disposed into the well. The fluorescent dye is sensitive to change in cell membrane potential in order to enable optical measurement of cell membrane potential. A $Na^+$ channel blocker, to be identified, is added to the well and a stimulating current is passed through the cell in an amount sufficient to generate an action potential before and after the addition of the $Na^+$ channel blocker. Thereafter, a change in cell membrane potential is optically measured. However the method is devoted to the identification of $Na^+$ channel blockers, and uses a conventional VSD approach to monitor $Na^+$ current upon $Na^+$ channel opening. The present invention is only intended for the study of sodium channel blockers, while stimulation is used in order to induce action potentials. WO 2007/041308 describes an apparatus and a method for detecting the activity of living cells. The system is able to sense the neuronal activity of living cells located in close proximity to an imaging sensor. There is a one-to-one correspondence between a detector array and an area sensed by the array: no optical lenses are interposed between the observed medium and the detector; no mirrors are used to modulate the light path, either. The present invention is not intended for drug screening and does not use electric stimulations.

Knöpfel T, et al. Methods. 2003 May; 30(1):42-8 discloses genetically targeted voltage-sensitive fluorescent proteins. This class of membrane voltage sensors overcomes previous limitations related to the nonselective staining of membranes associated with conventional voltage-sensitive dyes.

González J E, et al. Drug Discov Today. 1999 September; 4(9):431-439 is a review of relevant assay technologies for ion channels and describe voltage-sensitive probes and instruments based on fluorescence resonance energy transfer (FRET) that enable ion-channel drug discovery.

Dunlop J, et al. Comb Chem High Throughput Screen. 2008 August; 11(7):514-22 addresses the options available for cell-based screening of ion channels with examples of their utility and presents case studies on the successful implementation of high-throughput screening campaigns for a ligand-gated ion channel using a fluorescent calcium indicator, and a voltage-gated ion channel using a fluorescent membrane potential sensitive dye.

Dunlop J, et al. Nat Rev Drug Discov. 2008 April; 7(4): 358-68 provides an update on the current state-of-the-art for the various automated electrophysiology platforms that are now available and critically evaluates their impact in terms of ion-channel screening, lead optimization and the assessment of cardiac ion-channel safety liability.

DESCRIPTION OF THE INVENTION

The authors of the instant invention set a method for optically measuring variations in membrane conductance under conditions of controlled changes in the driving force for ion fluxes. More specifically, changes in the membrane conductance were evaluated by measuring the percent variation of the fluorescence emission of fast-VSD upon exposing a cell sample subjected to specific treatments to an electric current pulse, and comparing the results with those obtained from untreated cells exposed to the same electric current pulse.

Main limitation of fast-VSDs, as represented by their low sensitivity, are overcome by the method of the invention. The authors set up a method wherein traditional fast-VSDs are used, under proper conditions, as real-time sensors of membrane conductance. The method may be employed in HTS technology.

Upon application of proper electric current pulses, the cell membrane undergoes changes in the local transmembrane voltage that allow the extrapolation of membrane conductance through two basic parameters: i) the membrane time-constant charge/discharge or ii) the plateau value. Being directly related to the extent of membrane permeability, conductance measurements provide a direct method for quantifying the pharmacological profile of molecules able to directly or indirectly affect membrane permeability and is much more amenable to scalable technology than traditional electrophysiological techniques.

The method is applied to:
evaluate direct or indirect activation, modulation or blockade of ion channels or transporters expressed on the plasma membrane, with the possibility to derive experimentally a concentration-response relationship;
evaluate the direct permeabilizing effect of molecules with channel or transport characteristics (i.e. antibiotics);
evaluate changes in the basal conductance of the plasma membrane as a marker of the different physiological states of the cell.

The method can be proficiently exploited to:
perform high-throughput screening (HTS) and/or high-content screening (HCS) for drug discovery;
study the cellular and sub-cellular localization of permeability events in identified domains (even in complex and heterogeneous cellular models);

By this method it is possible to study any channel, independently of the way it is operated, of its specific permeability and of the extent of the ionic flux sustained by the electrochemical potential. Particularly interesting appears the possibility to study channels whose activity is prominent only under specific physiological conditions. Chloride channels are a good example since they play a major role when membrane potential is far from resting values. With the method of the invention, changes in membrane potentials can be imposed to force a redistribution of ions according to their electrochemical potential; in this way, it is possible to evaluate the activation of chloride channel independently of the physiological condition of the cell. Finally, the method is not limited to the study of specific channels or transporters but it is appropriate for the study of any condition leading to a change in permeability.

The steps of the method of the instant invention are:
a) Alteration of the Driving Force for Ion Fluxes Across the Plasma Membrane Changes in membrane potential are imposed by electric current pulses. This constitutes a technical improvement in term of exploitation of the moderate responsivity of fast-VSD since it promotes an amplification of the ionic currents flowing through the ion channels/transporters in a conductance dependent fashion.

b) Optimization of Signal Detection

Low fluorescence emission and sensitivity of commercially available fast-VSD are critical issues and were addressed by high-speed (up to 2000 frames per seconds) high-sensitivity video imaging (using most recent CCD and CMOS digital cameras), coupled to high resolution (typically 1 m) fluorescence microscopy.

c) Utilization of an Imaging System

The imaging system used to validate the invention was built around an inverted microscope equipped with:
532 nm laser as fluorescence excitation source with output power>30 mW;
"Plan-Apochromat" 40×, 1.3 N.A, oil-immersion objective lens;
dichroic filter;
band-pass emission filter centered at 650 nm (±10 nm);
a digital CMOS camera with integrated image intensifier for high frame rate (2000 images, 512×512 per second);
an intensified EMCCD camera (512×512) for best sensitivity.

The novel optical approach to measure changes in membrane conductance and perform HTS/HCS of molecules able to modify membrane permeability consists of the following steps:
expose one or more cells to an electric current pulse, by application of a current through electrode pairs with a precision<1 mA, to vary the membrane potential with respect to its resting value;
subcellular analysis of the variations of the membrane potential as changes in fast-VSD fluorescence before and during the electric current pulse;
convert variations of membrane voltage into values of membrane conductance, i.e. in a parameter that is function of the type and number of channels activated. More specifically, conductance is obtained by extrapolation of either time constant charge or steady state values of membrane charging.

Conductance values are measured under control conditions and after exposure to specific treatments. By comparison of the two values, it is possible to evaluate the effect of treatments on membrane permeability.

As a distinctive example of this approach, it is possible to draw pharmacological profiles for drugs or toxics acting, directly or indirectly, on ion channels. In this case, main advantages are:
any kind of channels can be studied;
no requirement for overexpression of the channel of interest;
comparable throughput and higher content with respect to available HTS (e.g FLIPR);

comparable content and higher throughput with respect to available HCS (e.g. automated electrophysiology approaches);

possibility of single cell and subcellular analysis.

The authors applied the method, obtaining the following results:

time course of changes in membrane conductance after triton X-100 administration;

concentration/response relationship in HeLa cells exposed to streptolysin-O;

capsaicin concentration-response relationship for CHO cells expressing VR1/TRPV1;

concentration-response curve for GABA in gabaergic differentiated Adult Neuronal Stem cells.

In conclusion, the authors set up an original approach to proficiently employ fast-VSD, fully exploiting their unsurpassed time resolution. The authors specifically propose a method for the rapid screening of candidate molecules able to affect membrane permeability (e.g. activation of ion channels) that is based on the estimation of the membrane conductance via analysis of the changes in the transmembrane potential (recorded by fast-VSD) when cell membranes are charged and discharged by electric current pulses. By this comprehensive approach, the pharmacological profile of molecules directly or indirectly acting on ion channels can be derived in individual cells and in subcellular compartments as well.

Therefore it is an object of the invention a method for measuring subcellular variations of the membrane conductance in a cell sample upon exposure to a compound or to a treatment, comprising the steps of:

a) labelling the plasma membrane of said cell sample with a voltage-sensitive dye, able to generate optically detectable signals indicative of local transmembrane potential with subcellular spatial distribution;

b) exposing said cell sample to an electric current pulse, wherein the total duration of the pulse is >20 milliseconds and its intensity is sufficient to evoke local transmembrane potential changes with no need to control their local intensity and spatial distribution;

c) acquiring at least one image of the optically detectable signals generated by the voltage-sensitive dye, before step b) and at last one image of the optically detectable signals generated by the voltage-sensitive dye, during step b) by means of an array of photo-detectors;

d) generating spatial maps of said local transmembrane potential changes of step b) by the optical images of step c);

e) evaluating local changes in membrane conductance by comparing spatial maps obtained in step d) of said cell sample exposed to said compound or to said treatment, with those obtained from a cell sample not exposed to the said compound or to the said treatment.

Step e) is obtained by one of the two following approaches:

by measuring the time constant values of transmembrane potential change from said maps of step d);

by measuring the amplitudes of transmembrane potential change from said maps of step d).

According to a preferred embodiment said voltage-sensitive dye is a molecule undergoing change in spectral properties as a consequence of membrane potential variation with a subsecond time response. Preferably said voltage-sensitive dye belongs to the group of molecules undergoing intramolecular charge redistribution. Alternatively said voltage-sensitive dye belongs to the group of molecules undergoing intramolecular Fluorescence Resonance Energy Transfer.

According to a preferred embodiment the labelling step a) is performed by exogenously administering the dye. Alternatively, the labelling step a) is performed by allowing the expression of a recombinant molecule within the cell sample.

According to a preferred embodiment said photo-detector belongs to the group of: charged coupled devices (CCD), complementary metal-oxide-semiconductors (CMOS), photodiode arrays with at least 40% quantum efficiency. The electric current pulse may be either monopolar or bipolar.

The term "quantum efficiency" refers to percentage of photons usefully detected with respect to the total number of photons that strike the detector.

According to a preferred embodiment said cell sample belongs to the group of: samples of biological tissue; cells dissociated from a biological tissue; cells from a eukaryotic cell lineage; genetically-engineered eukaryotic cells; cells from prokaryotic cell lineage.

According to a preferred embodiment said compound belongs to the group of molecules able of being incorporated into the plasma membrane altering plasma membrane permeability.

Alternatively said compound belongs to the group of molecules promoting, modulating or blocking the activity of non-voltage operated ion channels. Alternatively said compound belongs to the group of molecules promoting, modulating or blocking the activity of voltage operated ion channels. Alternatively said compound belongs to the group of molecules promoting, modulating or blocking the activity of ion transporters. Alternatively said compound belongs to the group of molecules promoting, modulating or blocking the incorporation of either new or recycling ion channels, and/or either new or recycling ion transporters.

The technical and scientific terms used hereafter have the same meanings as those commonly employed in the fields of fluorescence microscopy, molecular biology and cell imaging and are shortly defined as follows.

A "cell" refers to any type of cell, including cell lines, primary cultures or cells within tissue explants.

The term "subcellular" refers to a local or restricted area within a cell.

The term "membrane potential" or "transmembrane potential" refers to the electric potential difference across the plasma membrane of a cell.

The term "resting potential" refers to the membrane potential of a cell under steady state conditions, when not exposed to exogenous influences.

The terms "depolarization" and "hyperpolarization" refer to cases where the membrane potential changes from resting values in positive or negative directions respectively.

The term "driving force" for ion fluxes across the plasma membrane, refers to the electrochemical gradient able to drive individual ion species across the plasma membrane.

An "electrode" is a terminal capable of conducting electric current inwards or outwards.

The terms "monopolar" and "bipolar" refer to current pulses that respectively maintain the same polarity or undergo a switch of their polarity.

The term "fluorescence" refers to a phenomenon by which a compound, a molecule, a protein, a macro-molecular complex or a mixture of non-fluorescent and fluorescent compounds can absorb light ad a specific wavelength and emit light at a different wavelength over time.

The term "luminescence" refers to a phenomenon by which a compound, a molecule, a protein, a macro-molecular complex can absorb energy and then re-emit at least some fraction of that energy as light.

The term "FRET" stands for Fluorescence Resonance Energy Transfer, which refers to a process of energy transfer between two fluorophores.

An "optically detectable marker" refers to an agent that shows fluorescence, luminescence or FRET activity and can be detected by photosensors or photo-detectors.

A "voltage sensor" refers to an agent which is sensitive to voltage changes and can be used as indicator of membrane potential.

A "fast response voltage-sensitive dye (fast-VSD)" is an optically detectable marker, and a voltage sensor as well, capable to sense transitions of the membrane voltage on sub-second time scale.

The term "time constant" is the product of the membrane resistance times the membrane capacitance and express the charging properties of that specific membrane.

Advantages of the Instant Invention with Respect to the State of the Art in the Related Field

- Time resolution: the instant invention makes possible monitoring changes in membrane conductance (typically caused by drug acting on ion channels) on a millisecond time scale, i.e. two order of magnitude better than in conventional optical drug screening;
- Spatial resolution: the instant invention works at the sub-cellular level, thereby allowing the study of conductance changes in identified cells within heterogeneous populations as well as in subcompartments of cells with complex morphology;
- Sensitivity: the instant invention does not require overexpression of channels/transporters to have a proper readout of their activity;
- Specificity: the instant invention provides a highly specific readout with no restrictions on the nature of the molecular mechanism responsible for the change in conductance (in particular, it is open to the study of all ion channels with no limitations on the mechanisms of activation or to the ion species involved);
- Scalability: the instant invention makes cell-based high-content-screening compatible with the requirements of high throughput screening.

Figure 12:
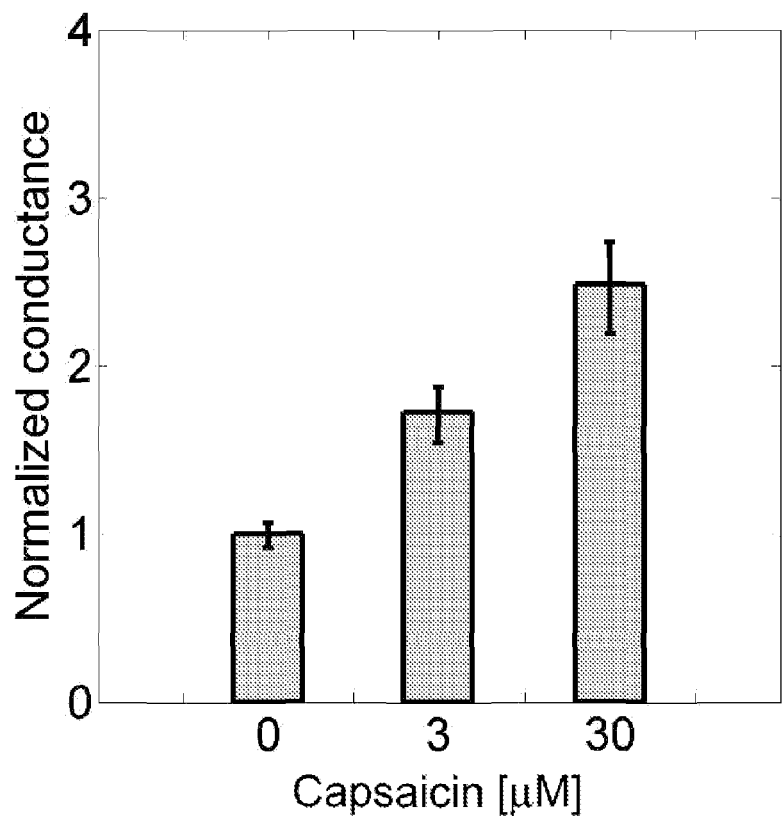
FIG. 12—Concentration-response relationship of capsaicin in CHO cells expressing VR1/TRPV1 (internal control). The response is expressed in terms of average conductance (internal control, see Materials and Methods). Value 1 corresponds to plasma membrane conductance in the absence of capsaicin. Error bars represent standard error of single cell measurements (n=20).

Conditions as in FIG. 12. Value 1 corresponds to plasma membrane conductance in the absence of GABA. Hill-coefficient=−0.314; EC50=0.71 kM.

DETAILED DESCRIPTION OF THE INVENTION

A biological membrane can be represented by an electrically equivalent circuit, in which a current can flow either across a capacitor (the lipid bilayer) or through ionic pathways (the ionic channels). Depending on the membrane model (purely resistive, purely capacitive or a combination of both), three different passive circuits can be envisaged. To investigate the time behaviour of such circuits, authors assumed a step-function current stimulation as input signal (switching from 0 to $I_S$ at time=0), and subsequently used standard analysis to derive the membrane voltage across the lipid bilayer from its transfer functions. The method is straightforward and leads to the analytical expressions in the time domain reported for each of the three cases, as drawn in FIG. 1.

Figure 1:
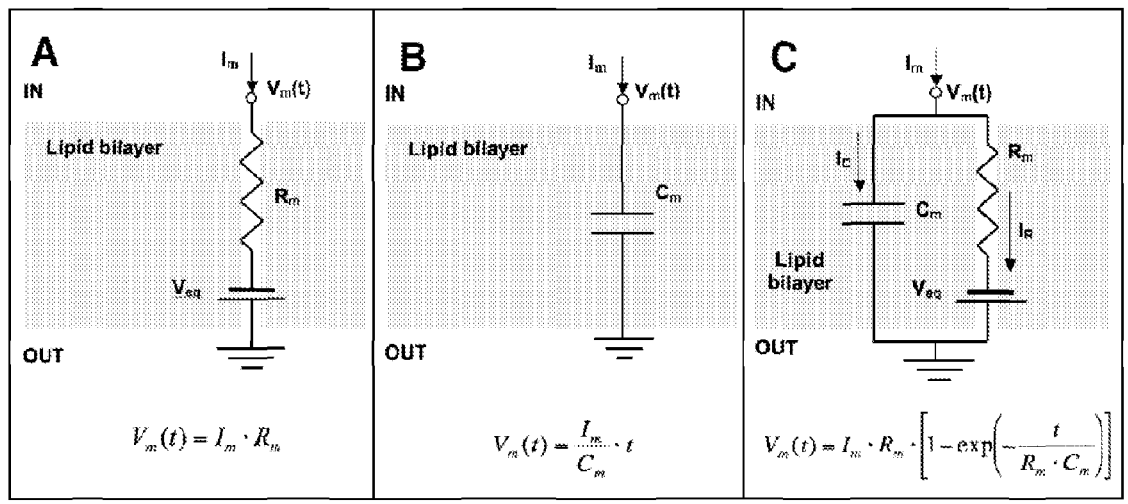
FIG. 1—Cell membrane models. A—Cell membrane modelled as purely resistive, composed of ion channels only. B—Cell membrane modelled as purely capacitive, composed of lipid molecules and no ion channels. C—Cell membrane modelled as a parallel R C circuit, composed of lipid molecules and ion channels FIG. 2—Simulation of a change in the conductance time courses of the membrane potential in the absence (A) and in the presence (B) of a conductance change coincident with the onset of the pulse.

The membrane potential of the resting cell reflects the compound electrochemical equilibrium potential for all the ionic species (which have different concentrations at the two sides of the membrane). Such "resting" potential is given, to a first approximation, by the contribution of the equilibrium potential of each species weighted by the permeability of the membrane to that species (Goldman's equation), and is represented in FIG. 1 by a battery ($V_{eq}$). Under the resting condition, $V_m = V_{eq}$ and the net current is zero. Whenever an additional constant current $I_S$ is supplied by an external source (a current generator), it distributes in the capacitive (capacitive current, $I_C$, changing the net surface charge of the membrane) and/or in the resistive branch (ionic current, $I_R$, carried by ions flowing through the channels), depending on the membrane potential value and the specific states of ion channels (activated or inactivated). At the onset of current application, the whole current flows through the capacitive branch ($I_C = I_S$), producing a change in membrane potential. As the membrane potential starts moving from its resting value ($V_{eq}$), the voltage difference across the membrane resistance makes current flow through the resistive branch. The resistive current increases until it equals the whole current across the membrane ($I_R = I_S$). This sets a new constant value for $V_m$, a condition under which no capacitive current occurs ($I_C = 0$).

The time course of the process just described follows an exponential time course with time constant $\tau_m$, which equals the product of the membrane capacitance $C_m$ times the membrane resistance $R_m$ (inverse of membrane conductance $G_m$):

$$\tau_m = R_m \cdot C_m = \frac{C_m}{G_m} \qquad 1)$$

Assuming that $C_m$ remains constant, $\tau_m$ is therefore directly proportional to membrane resistance $R_m$, and inversely proportional to $G_m$.

Let's now consider three basic situations, namely: 1) no change in membrane conductance (constant $R_m$), 2) change in membrane conductance between current pulses, 3) change in membrane conductance during current application.

1) Constant $R_m$—Regarding the steady state conditions, the application of the stimulating current $I_S$ moves the membrane potential from the resting value $V_m = V_{eq}$ (no net current) to a new equilibrium value $V'_m$ given by the sum of the electrochemical potential $V_{eq}$ and the product of $I_S$ times the resistance $R_m$:

$$V_m = V_{eq} \rightarrow V'_m = V_{eq} + I_S \cdot R_m \qquad 2)$$

If we now consider the transient between these two steady points, the time course of the process just described follows an exponential time course with time constant $\tau_m$, which equals the product of the membrane capacitance $C_m$ times the membrane resistance $R_m$ (inverse of membrane conductance $G_m$) (eq. 1).

2) Changes in $R_m$ between current pulses—If a change in membrane conductance occurs, and its time course is sufficiently rapid for the change to be complete before starting a new application of current $I_S$, the membrane potential will have moved from $V_m = V_{eq}$ to a value $V'_{eq}$ (the change in conductance generally modifies the relative permeability of the membrane to the various ions and therefore the electrochemical potential) before current application begins. Regarding steady state conditions, the application of $I_S$ will then move the membrane potential from $V_m = V'_{eq}$ to a value $V'_m$ which should reflect the new value of membrane resistance $R'_m$:

$$V_m = V_{eq} \rightarrow V'_m = V'_{eq} + I_S \cdot R_m \qquad 3)$$

This simply means that the steady displacement of the $V'_m$ value from its resting value $V'_{eq}$ equals the product of the supplied current times the membrane resistance $R'_m$ (inverse of its conductance $G'_m$):

$$V'_m - V'_{eq} = I_S \cdot R'_m = \frac{I_S}{G'_m} \qquad 4)$$

Therefore, the ratio between two membrane potential plateau displacements (referred to their own equilibrium value) will reflect the change in conductance, as shown in the following relation:

$$G_m \rightarrow G'_m \Rightarrow (V_m - V_{eq}) \rightarrow (V'_m - V'_{eq}) \qquad 5)$$

$$\Rightarrow \frac{(V'_m - V'_{eq})}{(V_m - V_{eq})} = \frac{I_S \cdot R'_m}{I_S \cdot R_m} = \frac{G_m}{G'_m}$$

As far as the time course of the process is concerned, under the assumption that the conductance change is completed before starting the current, its time behaviour is still exponential with time constant $\tau'_m$ given by the product of the membrane capacitance $C_m$ (assumed constant) times the new membrane resistance $R'_m$:

$$\tau'_m = R'_m \cdot C_m = \frac{C_m}{G'_m} \qquad 6)$$

Consequently, whenever $R_m$ changes, $\tau_m$ will be affected in the same manner, so that we can infer that the ratio between two time constants values $\tau_m$ and $\tau'_m$, measured at two different times, reflects a change in conductance:

$$R_m \rightarrow R'_m \Rightarrow \tau_m \rightarrow \tau'_m \qquad 7)$$

$$\frac{\tau'_m}{\tau_m} = \frac{R'_m C_m}{R_m C_m} = \frac{R'_m}{R_m} = \frac{G_m}{G'_m}$$

3) Changes in $R_m$ during current application—More complex situations occur if the membrane conductance changes during the application of a constant current $I_S$, which is equivalent to treat the membrane resistance as a time variable $R_m(t)$ even during current pulses. Under this condition, the membrane potential migrates towards a new steady-state value, which is the one appropriate to the new electrochemical potential and the new conductance.

It should be noted that this is not an uncommon situation, as voltage sensitive channels may open because of the voltage displacement produced by $I_S$ itself. Indeed, the aim of the experiment might be to investigate such channels.

In principle, two distinct possibilities can be envisaged:

a) The change in conductance is much faster than the membrane time constant $\tau_m$—The voltage displacement will reach a plateau, which is determined, as described above, by the combination of (i) the new conductance, and (ii) the change in equilibrium potential. Let's consider first the case where the conductance changes abruptly (it is considered instantaneous) at the very beginning of the current pulse. Looking at the time course of the membrane voltage $V'_m(t)$, we should expect an initial step-like change $\Delta V_{eq}$ due to the shift from $V_{eq}$ to $V'_{eq}$, followed by an exponential path with time constant $\tau'_m = C_m/G'_m$, where $G'_m$ represents the new value of membrane conductance. We can thus write:

$$G_m \to G'_m \Rightarrow \tau'_m = \frac{C_m}{G'_m} \Rightarrow V_{eq} \to V'_{eq} \quad 8)$$

$$\Rightarrow V'_m(t) =$$

$$V'_{eq} + \frac{I_S}{G'_m} \cdot \left[1 - \exp\left(-\frac{t}{\tau'_m}\right)\right] = V_{eq} + \Delta V_{eq} + \frac{I_S}{G'_m} \cdot \left[1 - \exp\left(-\frac{t}{\tau'_m}\right)\right]$$

$$V'_m(t \to \infty) - V_{eq} = \Delta V_{eq} + \frac{I_S}{G'_m}$$

Comparing this situation to that for which the conductance does not change (it remains equal to $G_m$), we obviously come to a conclusion analogous to that expressed by eq. 5:

$$G_m \Rightarrow V_m(t \to \infty) = V_{eq} + \frac{I_S}{G_m} \quad 9)$$

$$G'_m \Rightarrow V'_m(t \to \infty) = V'_{eq} + \frac{I_S}{G'_m}$$

$$I_S = const \Rightarrow \frac{V_m(t \to \infty) - V_{eq}}{V'_m(t \to \infty) - V'_{eq}} = \frac{G'_m}{G_m}$$

Figure 2:
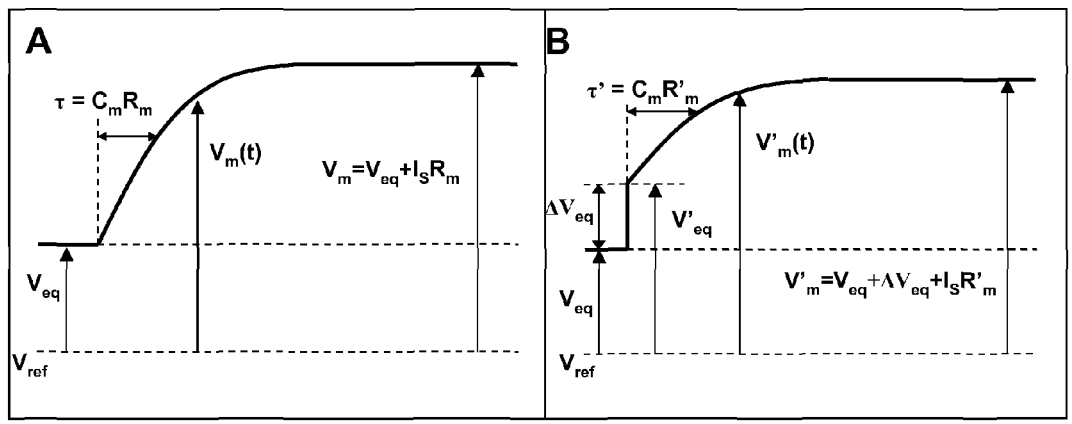

The graphs in FIG. 2 show schematically the time courses of the membrane potential for the two situations just considered, namely in the absence and in the presence of changes in membrane conductance.

Again, it is thus possible to estimate fractional changes in membrane conductance from the plateau displacements (referred to their own equilibrium value) or from the time constants of exponential changes ($G_m = C_m/\tau_m$, $G'_m = C_m/\tau'_m$).

Let's pass now to detail the situation in which the abrupt change of conductance (it is still instantaneous) occurs at a generic time $t=T$ during the current pulse.

We should still observe a step-like change $\Delta V_{eq}$ due to the shift from $V_{eq}$ to $V'_{eq}$, but now located at time $t=T$ instead of at the beginning of the pulse. This implies that the time course will show two different time constants $\tau_m$ (before conductance change) and $\tau'_m$ (after conductance change). Rigorously, we can write:

$$t = T; G_m \to G'_m \Rightarrow \tau_m = \frac{C_m}{G_m} \to \tau'_m = \frac{C_m}{G'_m} \Rightarrow V_{eq} \to V'_{eq} = V_{eq} + \Delta V_{eq} \quad 10)$$

$$0 \leq t < T \to V'_m(t) = V_{eq} + \frac{I_S}{G_m} \cdot \left[1 - \exp\left(-\frac{t}{\tau_m}\right)\right]$$

$$t = T \to V'_m(t) = V_{eq} + \Delta V_{eq} + \frac{I_S}{G_m} \cdot \left[1 - \exp\left(-\frac{T}{\tau_m}\right)\right]$$

$$t > T \to V'_m(t) = V_{eq} + \Delta V_{eq} + \frac{I_S}{G_m} \cdot \left[1 - \exp\left(-\frac{T}{\tau_m}\right)\right] +$$

$$\frac{I_S}{G'_m} \cdot \left[\frac{G_m - G'_m(1 - \exp(-T/\tau_m))}{G_m}\right]\left[1 - \exp\left(-\frac{t-T}{\tau'_m}\right)\right]$$

Figure 3:
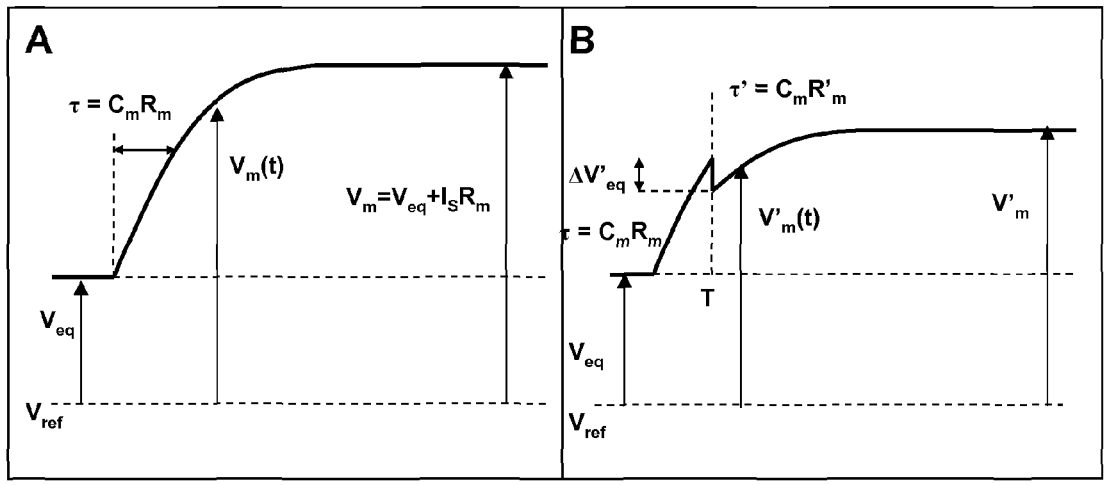
FIG. 3—Simulation of a change in the conductance time courses of the membrane potential in the absence (A) and in the presence (B) of a conductance change after the onset of the pulse.

The graphs in FIG. 3 show schematically the time courses of the membrane potential in the absence and in the presence of a conductance change during the current pulse (occurring at time $t=T$ in FIG. 3).

b) The conductance change occurs on a time-scale comparable to $\tau_m$ then the time course of the migration will be more complex and influenced by both the dynamics of channel opening and the membrane time constant $\tau'_m = C_m/G'_m$. Under these conditions, the mathematics become quite cumbersome, because both $V_{Eq}$ and $\tau'_m$ change with time according to a changing $G_m$. Thus, the changes in $\tau_m$ and in plateau $V_m$ displacement will not yield reliable quantitative estimates of the underlying conductance change, though they are still qualitatively—and semi-quantitatively—related to such changes, thereby constituting a means for detecting them and—to a limited extent—to describe their magnitude and approximate time course.

Figure 4:
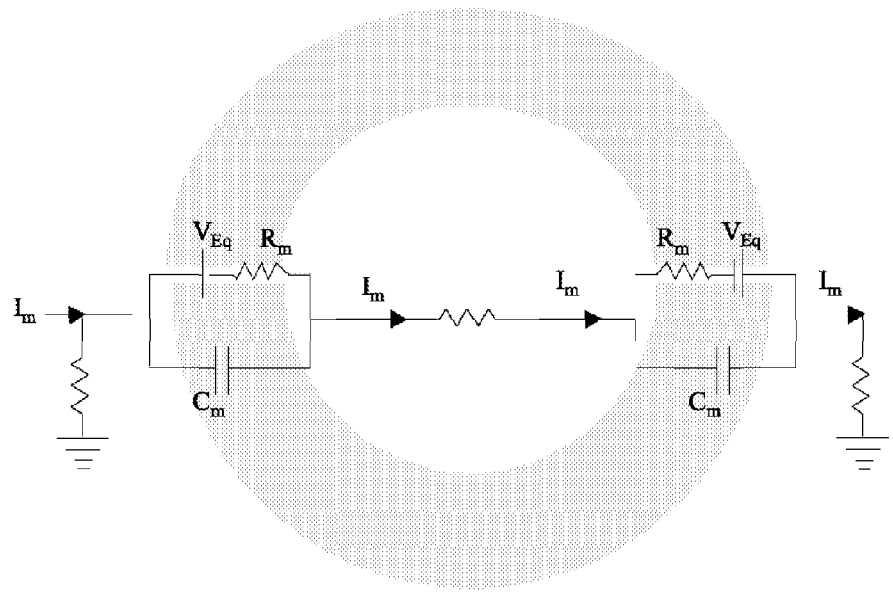
FIG. 4—Scheme of current flow in a cell exposed to an electric current pulse. The current crosses the membrane at the opposite sides of the cell with opposite direction. Accordingly, one side of the membrane is depolarised while the opposite side is hyperpolarised.

In general, however, there is a general aspect that makes it possible to deduce reliable information under these conditions: in dealing with changes in conductance that ensue in the ms time-scale during the application of current, it must be considered that such changes occur because voltage-dependent channels open in response to the displacement of membrane potential produced by the applied current. Under such condition, it is important to consider the whole cell as crossed by the current flow (as schematically illustrated in FIG. 4).

The current that crosses the membrane on one side of the cell also crosses the membrane of the opposite side, but with opposite direction (with respect to membrane polarization): thus, whereas one side of the membrane is depolarized, the opposite side is hyperpolarized. The activation of voltage-dependent channels and the related change in conductance will therefore occur on one but not the other side, and it will be possible to dissect it from the passive response of the membrane, by comparing the responses at the two opposite sides.

Methodology of Fluorescence Measurements

It is well established that each fast-VSD, due to its molecular rearrangement, is characterized by specific absorption and emission fluorescence spectra, which are shifted by a linear molecular Stark effect when subjected to an external electric field (electrochromism). If the fluorescence is measured in the region of the spectrum where emission is linear with wavelength, the change in fluorescence emission $\Delta F$ can be approximated by a linear function of the change of membrane potential $\Delta V_m$ (at least in the range of $\pm 100$ mV around its resting value).

The fluorescence emission at wavelength $\lambda$, under excitation at wavelength $\lambda_{ex}$, can be expressed, as shown in eq. 11 below, in terms of the excitation power $P_{ex}$, the efficiency of the optical system $E_{system}$, a smooth adimensional function $f(\lambda_{ex}, \lambda, V)$ of excitation and detection wavelengths (reflecting the specific spectral characteristics of the dye) and the bleaching time $\tau_{bleaching}$. The factor C is just a constant to account for dimension conversion.

It is worth mentioning that fluorescence bleaching can be well approximated by an exponential function over time intervals of 10 seconds or less, while for longer time excitations the time dependence of $\tau_{bleaching}$ should be taken into consideration.

$$F(\lambda, V, t) = C \cdot P_{ex} \cdot E_{system} \cdot \exp\left(-\frac{t}{\tau_{bleaching}}\right) \cdot f(\lambda_{ex}, \lambda, V) \quad 11)$$

During an experiment, sections of fluorescence measurement at fixed membrane potential V can be used to estimate the time course of dye bleaching, so that all the constants and the bleaching process can be grouped into a single time-varying function $\Phi(t)$:

$$\Phi(t) = C \cdot P_{ex} \cdot E_{sys} \cdot \exp(-t/\tau_{bleaching}) \quad 12)$$

Normalization of fluorescence measurements to this function compensates for bleaching and yields a corrected fluorescence measure $F_V$, which is solely function of potential and permits comparing values obtained at different time points during the experiment:

$$F_V = F(\lambda, V, t)/\Phi(t) = f(\lambda_{ex}, \lambda, V) \quad 13)$$

Following a change in potential, the fluorescence spectrum shifts slightly so that, provided that X is in a linear region of the spectrum, a corresponding variation $\Delta F_V$ of the normalized bleach-free function is observed:

$$\Delta F_V = \frac{df(\lambda_{ex}, \lambda)}{d\lambda} \cdot \frac{d\lambda}{dV} \cdot \Delta V_m \quad 14)$$

$$\frac{d\lambda}{dV} = const; \frac{df(\lambda_{ex}, \lambda)}{d\lambda} = const \Rightarrow \Delta F_V \propto \Delta V_m$$

It is worth reminding that the product $df/d\lambda \cdot d\lambda/dV$ is equivalent to the definition of dye sensitivity S.

So far, the analysis of the fluorescence signal did not include explicitly the membrane response to external electric stimulation, simply because fast-VSD emits in absence of electric fields as well ($F_0$). In resting conditions, the fluorescence emission $F_{eq}$ departs from $F_0$ linearly with the resting potential $V_{eq}$ (by the same arguments used in eq. 14), and such departure does not exceed about 4% for reasonable physiological values of $V_{eq}$.

As detailed above, the application of a step-function current stimulation induces charging of the cell membrane. This translates into a corresponding steady-state value F of the detected fluorescence signal (corrected for bleaching), which can be defined as:

$$F = F_{Veq} + \Delta F_V = f(\lambda_{ex}, \lambda, V_{eq}) + \frac{df(\lambda_{ex}, \lambda)}{d\lambda} \cdot \frac{d\lambda}{dV} \cdot I_S \cdot R_m \quad 15)$$

$$F - F_{Veq} = \frac{df(\lambda_{ex}, \lambda_{det})}{d\lambda} \cdot \frac{d\lambda}{dV} \cdot I_S \cdot R_m;$$

$$\frac{df(\lambda_{ex}, \lambda_{det})}{d\lambda} \cdot \frac{d\lambda}{dV} = const \Rightarrow F - F_{Veq} \propto I_S \cdot R_m$$

Therefore, the difference between the fluorescence steady-state displacement F during the current pulse and the baseline displacement $F_{Veq}$ is proportional to the membrane conductance. Instead of monitoring the fluorescence bleaching and computing the "bleach-free" function, $F_V$, the fluorescence signal during a relatively brief pulse of current can be normalised to the fluorescence signal prevailing immediately before the current pulse (at time $t=t_0$), so that we can conclude:

$$F(\lambda, V_{eq}, t) = \Phi(t) \cdot f(\lambda_{ex}, \lambda, V_{eq}) \quad 16)$$

$$F_{relative}(t) = \frac{F(\lambda, V_t, t_0 + t) - F(\lambda, V_{eq}, t_0)}{F(\lambda, V_{eq}, t_0)}$$

$$= \frac{\Phi(t_0 + t) F_{Vt} - \Phi(t_0) F_{Veq}}{\Phi(t_0) F_{Veq}}$$

$t \ll \tau_{bleach}$ $\Rightarrow \Phi(t_0 + t)$ $\approx \Phi(t_0)$ $\Rightarrow F_{relative}(t)$ $\approx \frac{F_V - F_{Veq}}{F_{Veq}}$ $= \frac{\frac{df(\lambda_{ex}, \lambda)}{d\lambda} \cdot \frac{d\lambda}{dV} \cdot (V - V_{eq})}{F_{Veq}}$ As $|F_{Veq} - F_0| < 0.04 \cdot F_0$, the denominator can be considered constant ($\approx F_0$), with the result that, in the linear region of the spectrum, we can write:

$$\frac{df(\lambda_{ex}, \lambda)}{d\lambda} = const; \frac{d\lambda}{dV} = const \Rightarrow F_{relative}(t) \propto V(t) - V_{eq} \quad 17)$$

The derivations of equations 16) and 17) are equivalent to apply a small perturbation approximation, which is crucial in assuring that the denominator can be considered independent of $V_{eq}$. This has been verified experimentally, and introduces an error not exceeding ±2% of $F_{relative}$.

It has been pointed out that changing the membrane conductivity moves $V_{eq}$ to a new value $V'_{eq}$, thus implying that the base line of fluorescence signal reaches a new equilibrium point. This should not affect relative fluorescence measurement, provided the conductance transient is already terminated before applying the stimulation current or it occurs instantaneously at the beginning of the current pulse.

CONCLUSIONS

1) Whenever a membrane conductance change occurs in between two successive applications of current, the membrane time constant shows an inverse relation to the membrane conductance, with the result that measuring the time constant of the fluorescence time course in response to the current pulse gives a quantitative (relative) analysis of membrane conductance.
2) Alternatively to method 1), it is possible to calculate the relative variation in conductance by performing the ratio between relative measurements of the fluorescence plateau displacements (referred to their own equilibrium values).
3) In case the conductance changes very slowly compared to the membrane time constant (seconds), it will be possible for statistical reason to apply more than one current pulse. This makes it possible to describe the time course of slow conductance changes produced by a drug or an experimental manoeuvre.
4) If the conductance change occurs during the current pulse, the above considerations still hold, provided that the change in conductance is much faster than the membrane time constant and the initial possible change in electrochemical potential is considered. If the change in conductance occurs on a time-scale comparable to τ, then it is mandatory to carefully compare the responses on the two opposite sides of the cell.

Being directly related to ion channel activity, conductance measurements provide a direct method for quantifying the pharmacological profile of molecules directly or indirectly acting on ion channels. In this way, it is possible to derive experimentally a dose-response curve concerning specific agonist/antagonist-receptor interactions by a procedure that follows channel activation kinetics and is much faster than prevailing optical approaches, coming close to the speed of traditional electrophysiological techniques.

Material and Methods

Before the experiment, cells were washed with a Krebs-Ringer's solution buffered with HEPES (KRH; in mM: 150 NaCl, 5 KCl, 1.2 MgSO4, 1.2 KH2PO4, 2 CaCl2, 10 glucose, and 10 HEPES, pH 7.4) and incubated with 2-10M di-4-ANEPPS, a fast-VSD (Invitrogen).

Figure 5:
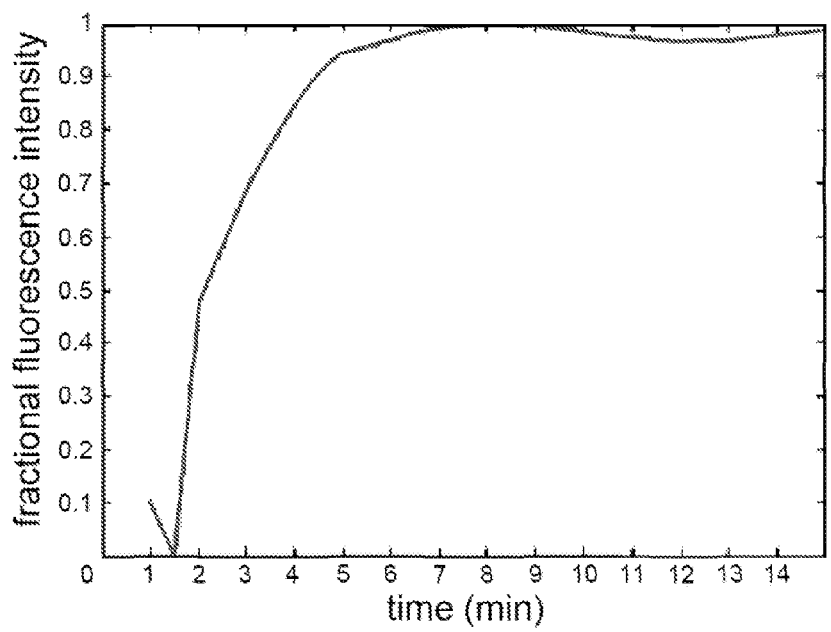
FIG. 5—Time course of di-4-ANEPPS loading, monitored as a function of the change in the intensity of fluorescence emission.

To be effective from the viewpoint of monitoring changes in fluorescence emission, dye molecules should be bound mostly on the plasma membrane. Unfortunately, the dye can be internalized by the cell, due to the physiological membrane turnover, with the result of being bound also to internal membranes, making them unresponsive to electrical stimulation. This problem was particularly relevant in CHO cells, so that, in order to minimize it, di-4-ANEPPS was loaded at 4° C. to highly reduce membrane traffic. Loading time was estimated as the time for fluorescence to reach a plateau (FIG. 5). Afterward, cells were transferred into the imaging system were it was possible to monitor changes in fluorescence and expose cells to electric current pulses.

Cell Cultures

HeLa cells were grown on plastic dishes at 37° C. in a 5% $CO_2$ humidified atmosphere in DMEM (Dulbecco's modified Eagle's medium) (BioWhittaker), supplemented with 10% fetal calf serum (Hyclone), 1% L-glutamine and 100 units/ml penicillin/streptomycin (BioWhittaker). Chinese Hamster Ovary cells (CHO) expressing the vanillod receptor-1 (VR1/TRPV1) were chosen because they represent a common model for high throughput screening. CHO cells were cultured in T75 cm$^2$ flasks in the following medium: DMEM/Nutrient MixF12 (GIBCO 31331-028) supplemented with: 1.35 mM sodium pyruvate (Euroclone, EC M0542D), 11 mM Hepes (Euroclone, EC M0180D), 0.2% sodium bicarbonate (Euroclone, EC M0980D), 10% FBS (Euroclone 0180L), 1% penicillin/streptomycin (Euroclone EC B3001D), 1% glutamine (Euroclone, EC B3000D) or ultraglutaminel (Cambrex, BE 17-605/U1), 100 mg/mL G418 (InvivoGen, cat.nr ant-gn-5).

ANS-1 cells were differentiated to GABAergic neuronal lineage by the procedure developed by Dialectica SpA. The differentiation process was reproducibly obtained by using an automated protocol of administration of DIFFKIT, a collection of media formulation to be applied at successive stages of neuronal differentiation. Briefly, BDNF is progressively added to the culture, while FGF-2 is progressively withdrawn.

In order to perform fluorescence experiments, cells were plated on glass coverslips. ANS-1 cells were directly grown and differentiated on coverslips. CHO and HeLa cells were split and plated on glass coverslips 2-3 days before the experiment date. Glass coverslips were precoated with Poly-L-Lysine (Sigma) overnight in 120 mM Borate Buffer pH 8.5.

Instrumentation

Current results were obtained by an imaging system built around an inverted microscope (Zeiss, Germany) equipped with:
- 532 nm laser as fluorescence excitation source with output power>30 mW;
- "Plan-Apochromat" 40×, 1.3 N.A, oil-immersion objective lens;
- dichroic filter (565 DCLP);
- band-pass emission filter centered at 640 nm (±20 nm);
- a digital CMOS camera with integrated image intensifier for high frame rate (up to 2000 images 512×512 per second) (Photron etc.);
- a digital back-thinned illuminated EMCCD camera for high quantum efficiency and signal-to-noise ratio.
- a stimulus generator with two electrodes Procedure On the whole, the measurement procedure comprises the following 7 steps:

Step 1—Preparing the cell cultures and subsequently staining them using fast-VSD markers.

Step 2—Exposing said cell cultures to light in order to excite fluorescence (Fluorescence excitation) and simultaneously acquiring, through a digital camera, repeated images of the optically detectable signal emitted by the fast-VSD molecules bound to the cell membrane. Each image can be regarded as a bi-dimensional array of photo-detectors (hereafter named pixels).

Step 3—Exposing said cell cultures to electric current pulses (Electrical stimulation) through a pair of electrodes, wherein the total duration of each pulse is >20 milliseconds and its intensity is high enough to evoke a significant trans-membrane potential change without directly affecting plasma membrane resistance.

Step 4—Time averaging of the values of fluorescence signal detected by each single pixel of the digital image (not corrected for fluorescence bleaching), where the actual number of samples will be equal to the actual number of images recorded.

Three distinct averaging need to be performed: 1) before stimulation, 2) during stimulation, 3) after stimulation. As results of such calculations, three separate values A1, A2 and A3 for each pixel should be obtained.

Step 5—Calculating the relative change of the fluorescence signal R, for each pixel of the array, as the ratio between the variations ΔF of detected signals and the baseline value F. Using parameters A1 A2 and A3, the parameter R will be given by the expression:

$$\Delta F = A_2 - \frac{(A_1 + A_3)}{2}$$

$$F = \frac{(A_1 + A_3)}{2}$$
$$\Rightarrow \frac{\Delta F}{F}$$
$$= \frac{A_2 - \frac{(A_1 + A_3)}{2}}{\frac{(A_1 + A_3)}{2}}$$
$$\Rightarrow R$$
$$\equiv \frac{\Delta F}{F}$$
$$= \frac{2A_2}{A_1 + A_3} - 1$$

Step 6—Filtering of images for the selection of subcellular areas whose pixels are representative of the cell response (see "Protocols for the measurement of cellular membrane conductance")

Step 7—From the results in step 6, a bi-dimensional array of values (one for each pixel of digital images) is available for further statistical analysis. We define the response parameter as the average of all absolute values of such array.

Application of Electric Current Pulses

According to our approach, cell membrane properties were investigated by fast-VSD before and during application of appropriate current pulses to the cells. This was accomplished by putting two electrodes in physical contact with the cell culture, and applying the required electric signals produced by a current generator. In the results here presented we used the following configuration:

two platinum electrodes with circular cross-section (0.7 mm), 5 mm length and 6.4 mm separation;

unipolar or bipolar square-shaped current pulses with duration>20 ms and intensity<150 mA;

The duration>20 ms proved adequate for the measurement of the membrane time-constant in the cells we investigated. Regarding the intensity of stimulation, the value was set high enough to generate detectable variations in fluorescence signal, without directly affecting membrane resistance.

Acquisition and Analysis of the Fluorescence Signals

Figure 6:
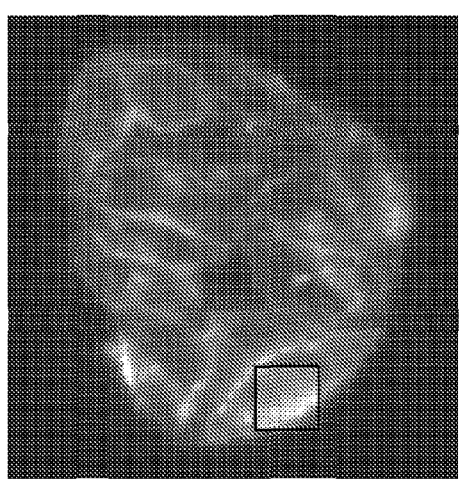
FIG. 6—Optical recording of membrane potential change evoked by electric current pulses. CHO cells loaded with fast-VSD (left panel) showed either positive or negative variations of the membrane potential, depending on the type of stimulus and on the geometry of the cells. Fluorescence intensity values (dots on the right graph) were measured within the square highlighted on the left. The time course of the change in membrane potential was fitted by a single exponential (line in the graph).
Figure 6:
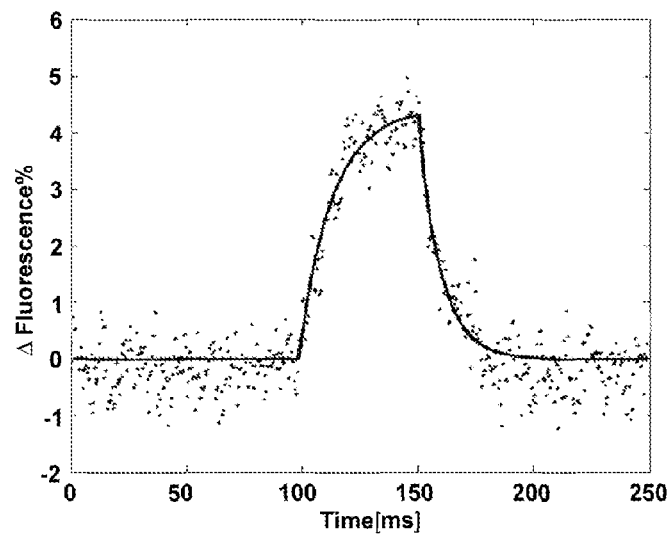

FIG. 6 shows a typical example of charging and discharging transients, obtained by exposing CHO cells to electric current pulses and detecting their fluorescence emission by the digital CMOS camera operating at 2000 images per second. In such experiment, 60 ms unipolar square-shaped current pulses were used. Fluorescence signals were recorded in the region highlighted by a square on the left. The graph on the right shows the effect of charging and discharging the membrane: each point refers to the percent fluorescence intensity change detected by the camera at 0.5 ms time intervals (one single image). In this way, it was possible to calculate the plateau values as well as the time-constants of membrane charge and discharge (calculated by single exponential fitting, line in the graph) from the time course of the evoked membrane potential change.

Protocols for the Measurement of Cellular Membrane Conductance

Conductance changes were monitored by measuring the change in fluorescence induced by electric current pulses, quantified as the difference between the mean of plateau values (either positive or negative, depending on the type of stimulus and geometry of the cell) and the mean of pre-stimulation values divided by the mean of pre-stimulation values, $\Delta F$ %. As detailed above, normalisation for the values prevailing before stimulation provided a correction for dye bleaching during the experiment, so that fluorescence changes produced by additional stimuli could be compared. Relative values thus obtained ($\Delta F$ %) linearly reproduce relative values of membrane potential displacement ($\Delta V$), which in turn are directly proportional to relative membrane resistance and inversely related to membrane conductance.

An increase in membrane conductance by exposure to permeabilizing agents or ionic channel agonists is expected to cause a reduction in evoked membrane potential changes (see "Rationale of the approach").

Typical digital images acquired in the instant invention comprise subcellular regions differentially responsive for morphological organization as well as spatial orientation with respect to the electrodes, and unresponsive background. In order to maximise the estimation of cellular responses, and consequent extrapolation of conductance measurement, selection of subcellular responsive areas is obtained by numerical filtering.

Figure 7:
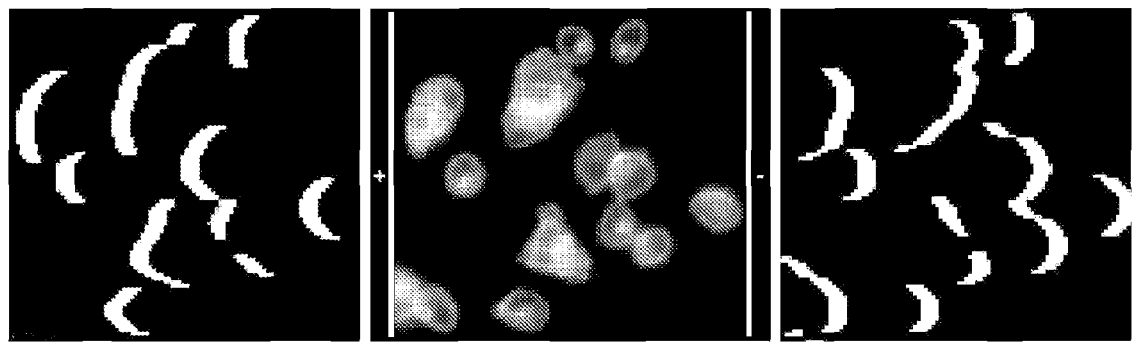
FIG. 7—"Left" and "right" morphological masks of a fluorescence image of CHO cells. Left and right panels show identified areas of individual cells facing anode and cathode respectively, in which positive and negative responses are expected (see "Material and Methods"). White bars in the central panel represent the position of electrodes (+ and −).

The following filters can be applied:

1) Identification of cellular areas and exclusion of background areas; 2) identification of the cell membrane regions with opposite responsiveness to the electric current pulse (see FIG. 7) 3); selection of pixels with response above a threshold.

The responsivity to the molecule active on membrane permeability was determined according to two different protocols:

Estimation of conductance with internal control (responses, before and after exposure to the experimental treatment, measured on the same pixels).

Typically, a functional mask was generated by selecting pixels with evoked membrane potential change higher than a certain threshold (at least 1% of rest values) under control conditions. This method ensures the unbiased selection of subcellular areas (portions of membrane) that, for geometrical reasons, respond to electric stimulation with significant changes in potential.

Afterward, membrane potential changes evoked by current pulses of fixed intensity were calculated within the same subcellular regions identified by the functional mask after exposure to the experimental treatment.

Individual pixels responsivity was measured as the fractional variation of the evoked membrane potential change after the experimental treatment with respect to the control.

The responsivity to the experimental treatment (change in conductance) was expressed by a numerical value that represents the average of individual pixels responsivities.

Estimation of conductance with external control (responses before and after exposure to the experimental treatment are measured on independent samples).

Typically, two morphological masks were generated for each analyzed field in order to separate positive from negative signals. More specifically, pixels were selected when the following requirements were met: to be part of the cell (recognition of object boundary from fluorescence signals); to be confined to the plasma membrane region (calculation of a ring of depth boundaries); to be geometrically confined with respect to the axis of stimulation (the central half of either one or the other of the two opposite sides of individual cells; see FIG. 7). Since these two extreme sides of the cells are expected to have responses of opposite sign to the same stimulus, the two masks separate the two different contributions.

The average evoked membrane potential change was calculated for all pixels in "left" and "right" masks in the control preparations as well as in those exposed to the active molecule (independent samples).

Responsivity of subcellular areas to the experimental treatment (change in conductance) was expressed by a numerical value that represents the fractional variation of the average evoked membrane potential change after administration of the active molecule with respect to the control.

Determination of the Concentration-Response Relationship

Molecules directly or indirectly affecting membrane permeability were applied to cells. A time course of the effect of these molecules (change in resistance/conductance) was first performed using maximal concentrations to determine the pre-incubation time necessary to achieve the full response. Afterward, various concentrations were administered for the proper time, not in sequence to the same cells, but in distinct wells to avoid receptor-specific desensitization, which depends on sustained agonist binding. Responsivity to the agonist was evaluated as described above. To increase the reliability of the measurements, each experimental point represents the average of multiple measurements of cellular membrane conductance in either the same or different fields. Values were then normalised to basal conductance: values above 1 indicate added conductance, presumably due to pore formation (or endogenous channel activation) by the drug, whereas values<1 indicate block of endogenous conductances.

Results

Set Up Of Fast-VSD Loading Procedure

The loading time for fast-VSD is a critical parameter:
to allow the dye to efficiently bind to the outward surface of the cell membrane, while minimising its internalization with the consequence of having a bias of unresponsive VSD fluorescence;
to ensure the highest possible fluorescence signal, for best signal-to-noise ratio, while reducing as much as possible the exposure to the excitation light and its ensuing phototoxic effects on cells.

The graph in FIG. 5 shows the fluorescence intensity as a function of di-4-ANEPPS loading time; the time-trace reveals that 8 minutes were sufficient to reach maximal fluorescence intensity. This loading time was adopted in all experiments. When performed at 4° C., loading time was extended to 10 minutes.

Effects of Electric Current Pulses in Control Cells

Figure 8:
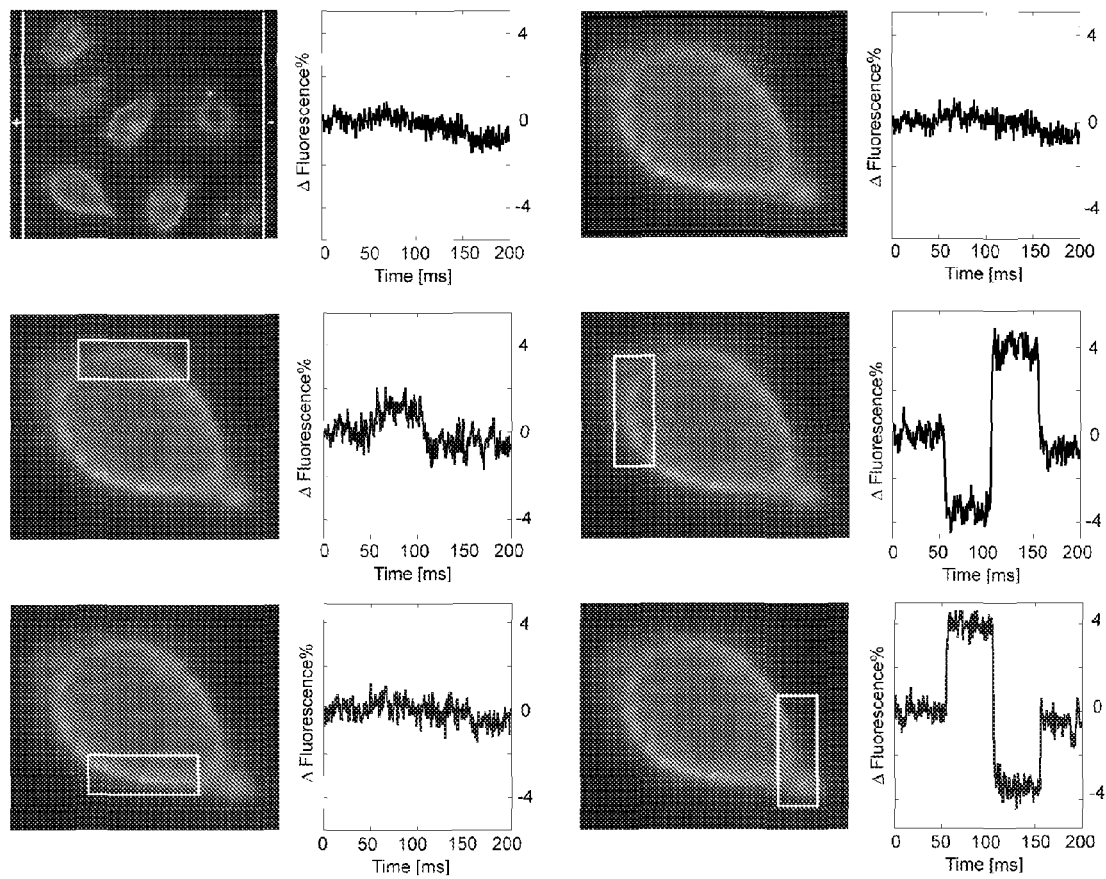
FIG. 8—Fluorescence intensity changes (% of prepulse intensity) recorded in different subcellular regions (highlighted by squares) of a single HeLa cell exposed to a bipolar current pulse. The average signal from the whole field (upper left panel) or even from an entire cell (upper right panel) shows virtually no variations upon stimulation. Similarly, small or no variations are observed when plasma membrane is perpendicular with respect to the electrodes (left middle and left bottom panels). Significant variations are observed only when plasma membrane is parallel to the electrodes (middle and lower panels on the right); notice that when one side is depolarized the opposite is hyperpolarized and viceversa). White bars in the up-right panel represent electrodes.

The use of electric current pulses offers the possibility to study many cells simultaneously, but at the price of generating changes in membrane potential with non-uniform spatial distribution. Depending on cell geometry and on their position/orientation with respect to electrodes (anode and cathode), the angle between electric field lines and the dipole moments of dye molecules, changes in space. Accordingly, variations of membrane potentials are angle-dependent and reverse their sign when moving from the edge of the cell facing the anode to the edge facing the cathode. FIG. 8 schematically shows the behaviour of a single cell subjected to bipolar current pulses: hyperpolarisation (deflection toward higher values) is seen on the side facing the anode and depolarisation (deflection toward lower values) on the side facing the cathode, while no effect is expected in directions perpendicular to electric field lines. Switching the direction of the applied electric current is expected to reverse the fluorescence changes in the cell.

It follows that the study of the signals evoked by electric current pulses requires sub-cellular analysis.

The protocols we employed in this work to study membrane conductance start from the assumption that the channels under investigation are ohmic (I/V relation is linear). Accordingly, positive and negative values can be treated in the same way. In the case of ion channels activated (or closed) by the change in potential produced by the applied current, the changes in conductance produced by a hyper- or a depolarisation may markedly differ (for most channels, no change will be produced by hyperpolarisation from resting conditions, while an increase of conductance will be produced by a sufficiently intense depolarisation). Under these conditions the positive and negative changes in membrane potential should be analysed separately, and their comparison will yield precious information on the amplitude and time course of the conductance change produced by the supplied current crossing the membrane in one but not in the other direction.

Figure 9:
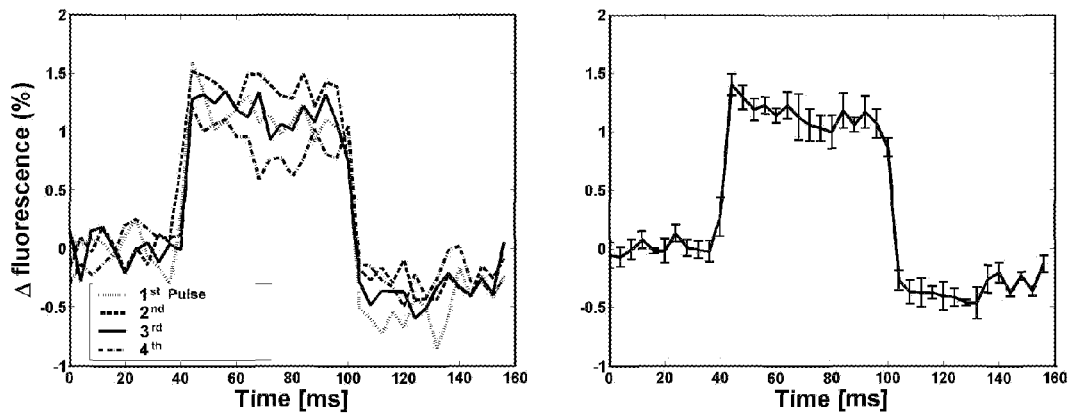
FIG. 9—Fast-VSD responses to unipolar electric current pulses in HeLa cells. High reproducibility of plateau values was observed on a membrane portion when the same stimulus (square pulse) was applied four times with 10 s interval between pulses. On the right the averaged profile of the four responses. Bars represent standard deviation.

In order to test the reproducibility of the evoked membrane potential changes, the same stimulus was applied after adequate interval to allow cells to recover (FIG. 9).

Responses were highly reproducible, when cells were allowed to recover.

Optical Detection of Changes in Membrane Conductance Induced by Aspecific Permeabilization Triton X-100 is a detergent commonly used in biology to disrupt membranes of eukaryotic cells. At low concentrations, its activity of lipid extraction is not strong enough to kill cells; rather, equilibrium is reached, in which cells are still alive, even though their outer membranes show a degree of permeability to ions higher than normal. Since triton X-100 activity is straightforward on the membrane (i.e. it requires neither membrane channels nor any other specific structure, beside the leaky lipidic bilayer itself, to have an effect), it was used to demonstrate the possibility of optically evaluating changes in membrane permeability. In particular, TritonX-100 was expected to lower membrane resistance (i.e. an increase in conductance) in a dose dependent manner. Low frequency current pulses (4 unipolar square waves of 52 ms in duration and 80 mA in amplitude per minute, FIG. 10) were applied. Fast-VSD optical signals (512×512 pixel images, 500 Hz acquisition rate) were recorded in two time-windows of 40 ms: the first before electric stimulation, the second during the plateau phase of the response to the current pulse. In order to obtain reliable responses, measurements were performed in regions in which control fast-VSD changes had been >1% (functional mask, see Material and Methods).

Since triton X-100 is expected to have a progressive action in permeabilising the membrane, reaching a plateau at equilibrium, measures were performed up to four minutes after administration. Changes in cell membrane conductance were calculated by applying the protocol for the estimation of conductance with internal control, in which responses, before and after exposure to triton X-100, are measured on the same sample (see "Material and Methods").

Figure 10:
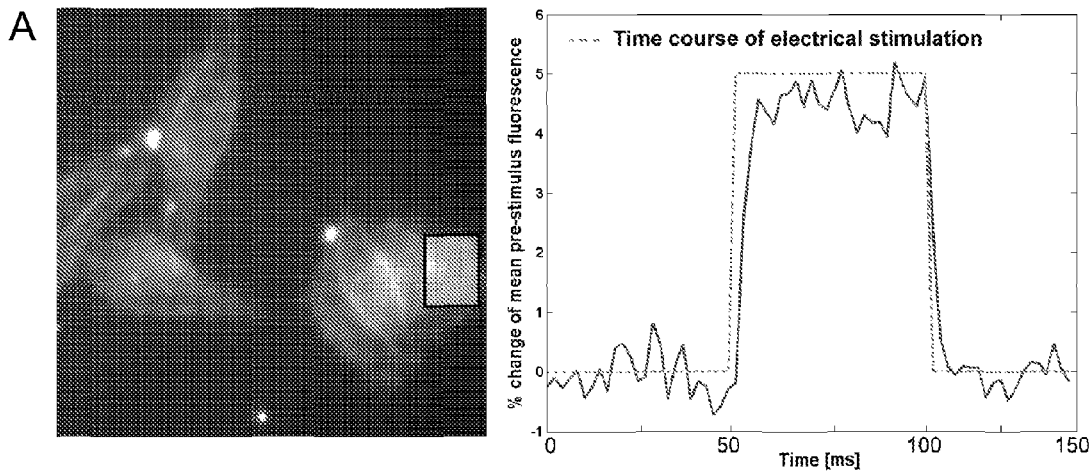
FIG. 10—Optical detection of changes in the membrane conductance of HeLa cells exposed to triton X-100. A: on the left: fluorescence image of HeLa cells observed in the experiment. Mean intensity values within the region of interest (highlighted by the square) are graphed on the right (continuous line). The superimposed dashed line represents the electrical stimulus. B: time course of changes in membrane conductance (conductance normalised to the value at time t=0) at rest and after administration of triton X-100.
Figure 10:
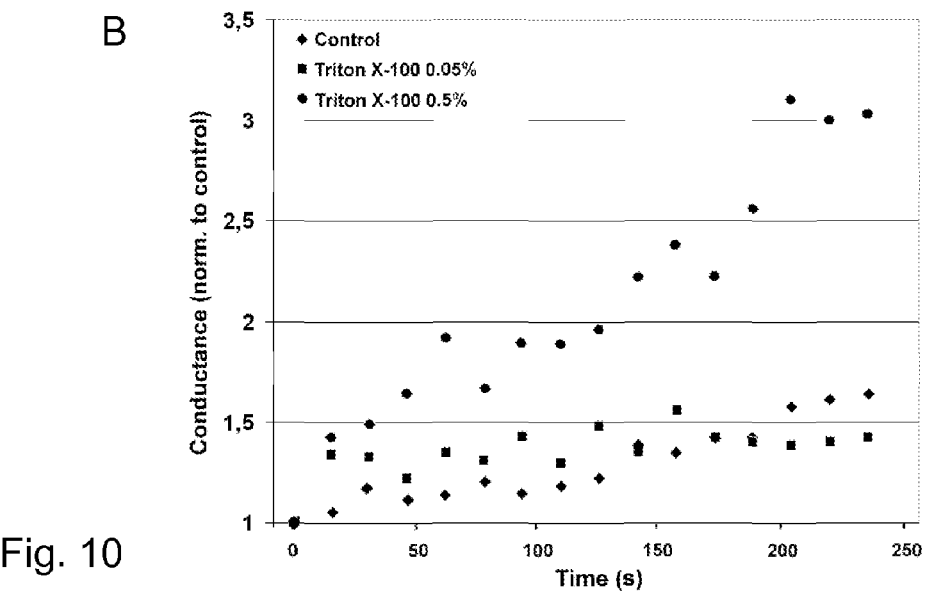

FIG. 10 illustrates the time course of changes in membrane conductance after triton X-100 administration. A slight, time-dependent reduction in the response was observed in the control experiment; this can be ascribed to the effect of the repetitive stimulation protocol itself (which was devised to follow the activity of triton X-100). A low concentration of Triton (0.05% volume) had a negligible effect on membrane conductance while a higher concentration (0.5% volume) produced a marked drop.

Figure 11:
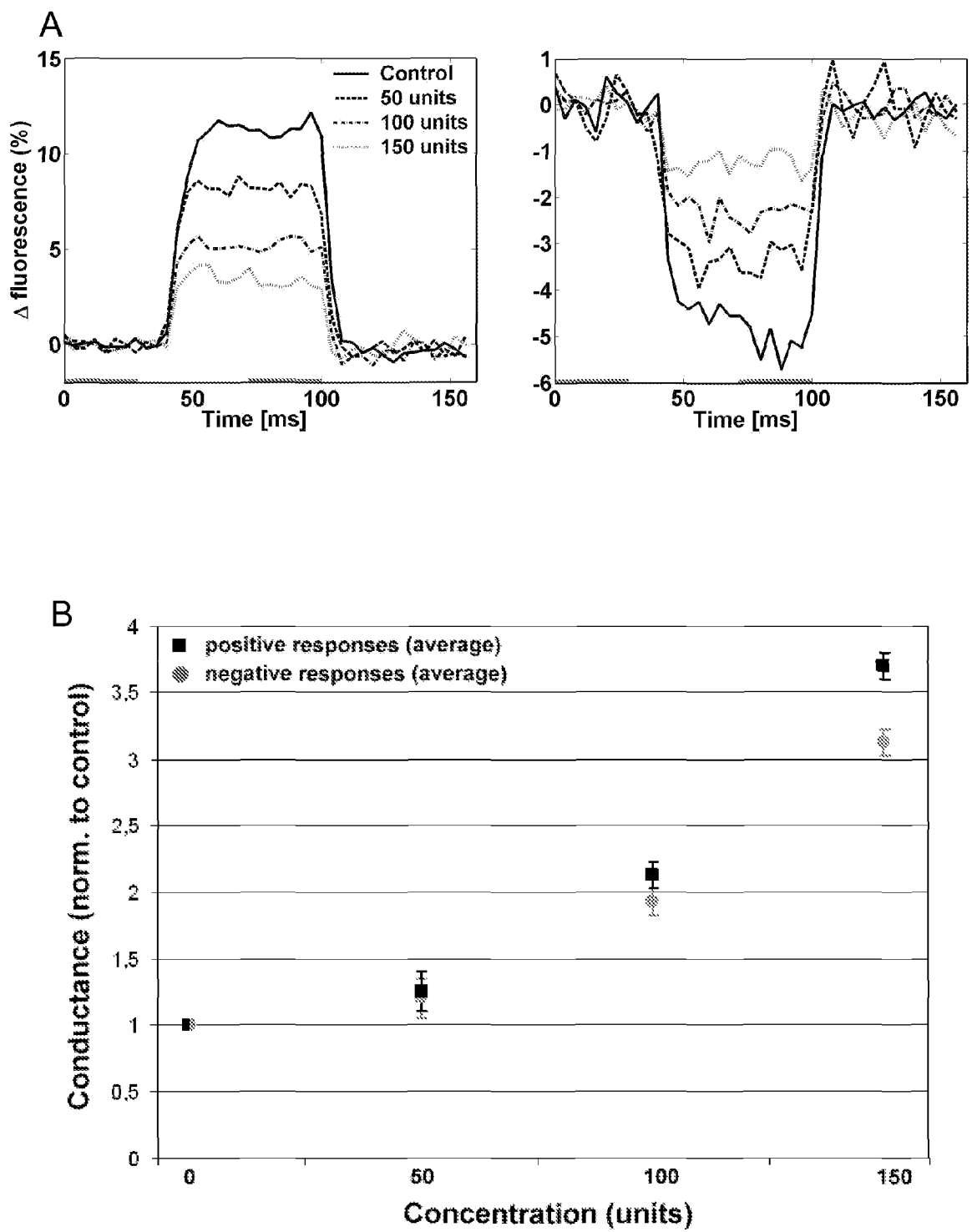
FIG. 11-Optical detection of changes in plasma membrane conductance of HeLa cells exposed to streptolysin-O. A: Fast-VSD variations recorded during stimulation with a unipolar square pulse in the absence or presence of different streptolysin-O concentrations; hyperpolarising (left) and depolarising (right) responses are shown. Under both conditions, there is a clear reduction in the fluorescence variation when concentration of streptolysin-O is increased. Gray bars indicate the time-windows used for conductance measurement. B: Changes in conductance (normalised to the control value) after administration of increasing concentrations of streptolysin-O are shown for both positive and negative variations. Bars represent standard errors.

Optical Detection of the Changes in Membrane Conductance Induced by Strepolysin-O Streptolysin-O is a bacterial protein able to insert into the eukaryotic plasma membrane where it forms a non selective ionic channel. A direct consequence of the presence of these channels is a change in membrane permeability. Accordingly, this is a simple model to challenge the ability of our methodology to test membrane conductance variation in a concentration dependent manner. HeLa cells were exposed to increasing concentrations of streptolysin-O and our protocol for the estimation of conductance with internal control was applied (see Material and Methods). Low frequency current pulses (4 unipolar square waves of 60 ms in duration and 80 mA in amplitude per minute) were applied. Fast-VSD optical signals (512×512 pixel images, 500 Hz acquisition rate) were recorded in two time-windows of 30 ms: the first before the electric current pulse, the second during the plateau phase of the response to the current pulse (see FIG. 11). Measurements were performed using the functional mask (control fast-VSD changes>2%). An example of the plateau variations in a cellular region after streptolysin-O addition is shown in FIG. 11.

The amplitude of the responses to increasing concentration of streptolysin-O (50, 100 and 150 units) were measured and compared with the amplitude of the control responses within the same region of the cell. The relationship between streptolysin-O concentration and the increase in membrane conductance is in line with the expectations of the method.

Determination of a Concentration-Response Relationship for Capsaicin in Chinese Hamster Ovary (CHO) Cells Expressing Vanilloid Receptor-1 (VR1/TRPV1) (Use of the Protocol with Internal Control)

Vanilloid receptors are activated by different stimuli, one of which is capsaicin, the active ingredient of green pepper, an alkaloid irritating to the skin and mucous membranes. In this series of experiments, we employed our approach to evaluate a concentration-response relationship for capsaicin in CHO cells engineered to express vanilloid receptor-1 (VR1/TRPV1), a non-selective cation channel. Pre-incubation time was 3 min in all experiments. CHO cells were exposed to increasing concentrations of capsaicin and our protocol for the estimation of conductance with internal control was applied (see Material and Methods). Low frequency current pulses (3 bipolar square waves of 50+50 ms in duration and +/−100 mA in amplitude per minute) were applied. Fast-VSD optical signals (512×512 pixel images, 500 Hz acquisition rate) were recorded in two time-windows of 30 ms: the first before electric current pulse, the second during the steady-state phases of the response to the current pulse. In order to obtain reliable responses, measurements were performed in regions with control fast-VSD changes>2% (functional mask, see Material and Methods).

Each experimental point represents the average of three measurements of cellular membrane conductance in the same field. The experimental concentration-response relationship is illustrated in FIG. 12.

Determination of Concentration-Response Relationship for Capsaicin in Chinese Hamster Ovary (CHO) Cells Expressing Vanilloid Receptors (Use of the Protocol with External Control)

To evaluate the possibility of studying variations in the responsivity of cells to electric current pulse after drug action, without using the same cells as control (with a technical and methodological simplification with respect to the "internal control" method), we repeated one of the previous experiments by using different samples for the various concentrations of the agonist as well as for the control. However, this also implies that it was not possible to use a functional mask to confine the analysis to responsive pixels and that it was necessary to adopt a morphological mask (see "Material and Methods"). Therefore, we determined a concentration-response relationship for capsaicin in CHO cells expressing VR1/TRPV1 under the same experimental conditions previously described with the following differences:

controls were from independent samples;
a morphological mask was used;
each experimental point represents the average of stimulations in 5 different fields.

Figure 13:
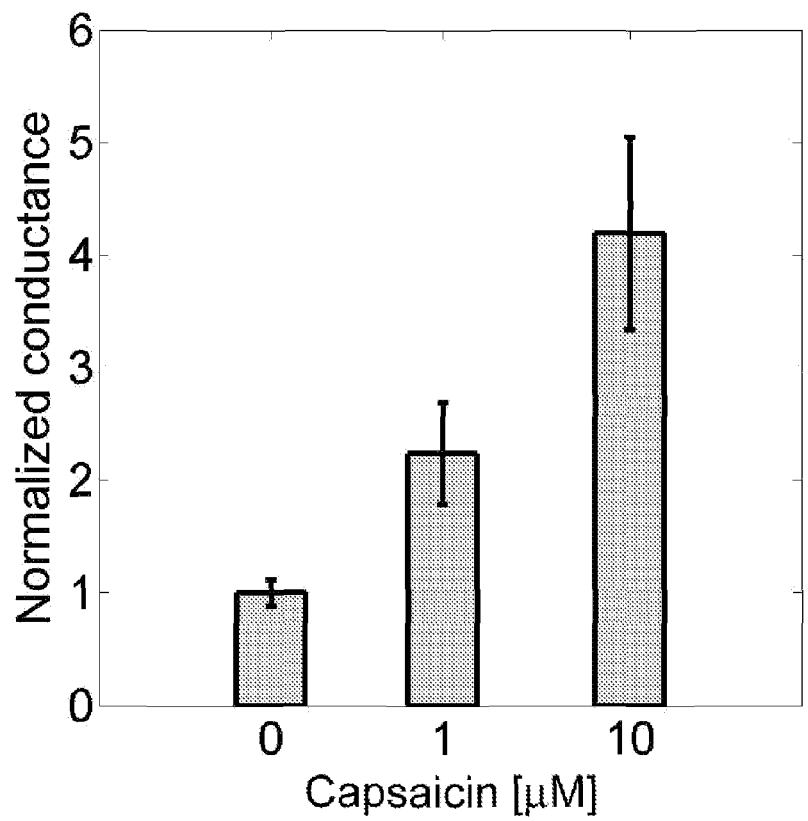
FIG. 13—Concentration-response relationship for CHO cells expressing VR1/TRPV1 (external control). Conditions are as in FIG. 12, with the difference that an external control was used (see details in Material and Methods). Value 1 corresponds to plasma membrane conductance in the absence of capsaicin. Error bars represent standard errors of single field measurements (n=5).

The experimental concentration-response relationship is illustrated in FIG. 13.

Determination of Dose-Response Curve for γ-Amino-Butyric Acid (GABA) in Adult Neuronal Stem (ANS) Cells (Use of the Protocol with Internal Control)

Neuronal Stem (NS) cells are cells with neurogenic radial glia-like properties by morphology and molecular markers. These cells can be long-term homogeneously expanded in adherent conditions maintaining indefinitely the potential capacity to generate both neurons and astrocytes. ANS-1 cells are NS cells derived from adult mouse SubVentricular Zone1 that can be differentiated to a neuronal lineage up to complete neurochemical and electrochemical maturation. In particular, ANS-1 differentiated neurons express a gabaergic phenotype, being endowed with GABAA receptors, anionic channels that upon activation let chloride ions flow. Pre-incubation time was 3 min in all experiments. ANS-1 neurons were exposed to increasing concentrations of GABA and our protocol for the estimation of conductance with internal control was applied (see Material and Methods). Low frequency current pulses (3 unipolar square waves of 48 ms in duration and 60 mA in amplitude per minute) were applied. Fast-VSD optical signals (512×512 pixel images, 250 Hz acquisition rate) were recorded in two time-windows of 25 ms: the first before electric current pulse, the second during the plateau phase of the response to the current pulse. In order to obtain reliable responses, measurements were performed in regions with control fast-VSD changes>2% (functional mask, see Material and Methods).

Figure 14:
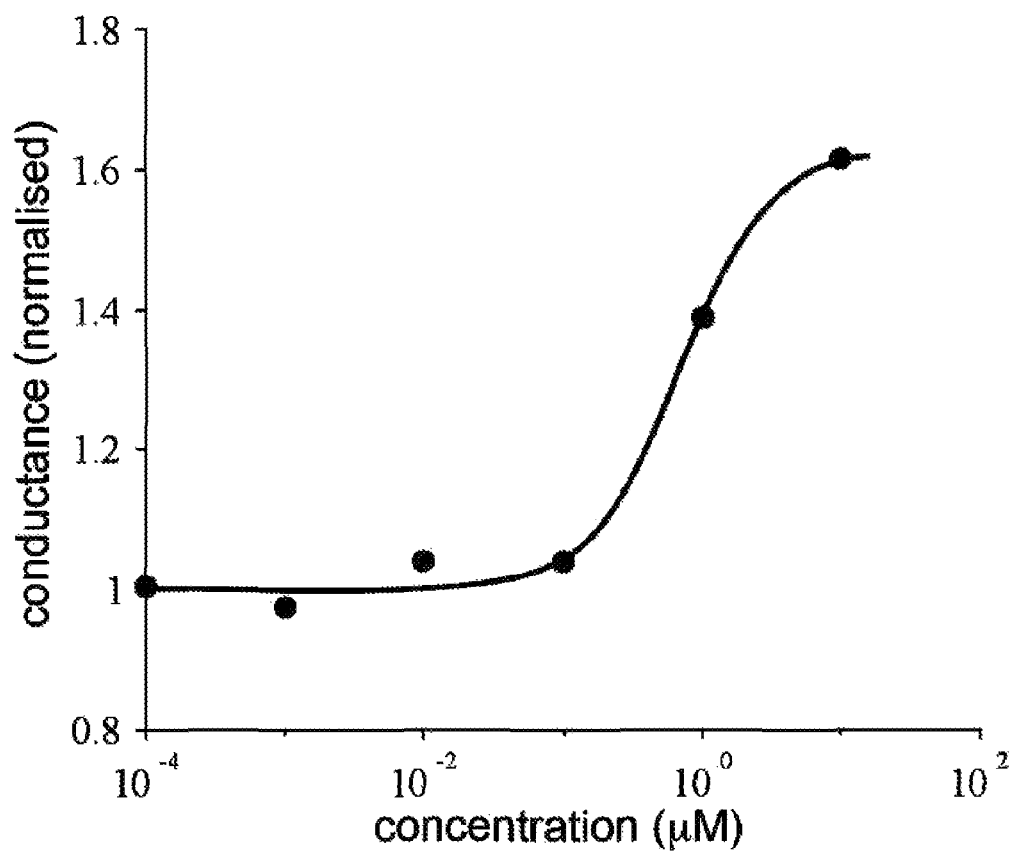
FIG. 14—Concentration-response curve of GABA in ANS-1 cells expressing GABAA receptors (internal control).

Each experimental point represents the average of three measurements of cellular membrane conductance in the same field. From the series of concentration we tested it was possible to derive an experimental concentration-response curve (FIG. 14). The result is in line with the concentration-response relationship obtained with the automated patch clamp systems QPatch (Sophion Bioscience, Denmark) from the ligand-gated ion channel hGABAA receptors expressed in HEK-293 cells and shown on their site (sophion.dk/sophion/pdf/reports/AR13781%20-%20PrecisIONTM %20Gaba-a.pdf).

The invention claimed is:

1. A method for measuring subcellular variations of the membrane conductance in a cell sample upon exposure to a compound, comprising the steps of:
    a) labelling the plasma membrane of said cell sample with a voltage-sensitive dye, able to generate optically detectable signals indicative of local transmembrane potential with subcellular spatial distribution;
    b) exposing said cell sample to an electric current pulse with a constant current generator, wherein the total duration of the pulse is >20 milliseconds and its intensity is sufficient to evoke local transmembrane potential changes with no need to control their local intensity and spatial distribution;
    c) acquiring at least one image of the optically detectable signals generated by the voltage-sensitive dye, before step b) and at least one image of the optically detectable signals generated by the voltage-sensitive dye, during step b) by means of an array of photo-detectors;
    d) generating spatial maps of said local transmembrane potential changes of step b) by the optical images of step c);
    e) exposing said cell sample labeled in step a) to said compound;
    f) conducting said steps b), c), and d) on said cell sample exposed to said compound; and
    g) evaluating local changes in membrane conductance by comparing spatial maps obtained in step d) of said cell sample not exposed to said compound, with those obtained in step f) from said cell sample exposed to said compound.

2. The method of claim 1, wherein in step g) the evaluation of local changes in membrane conductance is obtained by measuring the time constant values of transmembrane potential change (tau value) from said maps of step d).

3. The method of claim 1, wherein in step g) the evaluation of local changes in membrane conductance is obtained by measuring the amplitudes of transmembrane potential change (plateau value) from said maps of step d).

4. The method of claim 1 wherein said voltage-sensitive dye is a molecule undergoing change in spectral properties as a consequence of membrane potential variation with a sub-second time response.

5. The method of claim 4, wherein said voltage-sensitive dye belongs to the group of molecules undergoing intramolecular charge redistribution.

6. The method of claim 4, wherein said voltage-sensitive dye belongs to the group of molecules undergoing intramolecular Fluorescence Resonance Energy Transfer.

7. The method of claim 1, wherein the labelling step a) is performed by exogenously administering the dye.

8. The method of claim 1, wherein the labelling step a) is performed by allowing the expression of a recombinant molecule within the cell sample.

9. The method of claim 1, wherein said array of photodetectors is selected from the group consisting of: charged coupled devices (CCD), complementary metal-oxide-semiconductors (CMOS), and photodiode arrays.

10. The method of claim 1, wherein said electric current pulse is monopolar.

11. The method of claim 1, wherein said electric current pulse is bipolar.

12. The method of claim 1, wherein said cell sample is selected from the group consisting of: samples of biological tissue; cells dissociated from a biological tissue; cells from a eukaryotic cell lineage; genetically-engineered eukaryotic cells; and cells from prokaryotic cell lineage.

13. The method of claim 1, wherein said compound belongs to the group of molecules able of being incorporated into the plasma membrane altering plasma membrane permeability.

14. The method of claim 1, wherein said compound belongs to the group of molecules promoting, modulating or blocking the activity of non-voltage operated ion channels.

15. The method of claim 1, wherein said compound belongs to the group of molecules promoting, modulating or blocking the activity of voltage operated ion channels.

16. The method of claim 1, wherein said compound belongs to the group of molecules promoting, modulating or blocking the activity of ion transporters.

17. The method of claim 1, wherein said compound belongs to the group of molecules promoting, modulating or blocking the incorporation of either new or recycling ion channels, and/or either new or recycling ion transporters.

* * * * *